United States Patent
Sasada et al.

(12)

(10) Patent No.: US 6,183,971 B1
(45) Date of Patent: Feb. 6, 2001

(54) HUMAN BETACELLULIN-SPECIFIC ANTIBODIES AND USES THEREOF

(75) Inventors: Reiko Sasada, Kyoto; Tatsuya Watanabe, Osaka; Yukio Toyoda, Hyogo, all of (JP)

(73) Assignee: Takeda Chemical Industries, Ltd., Osaka (JP)

( * ) Notice: Under 35 U.S.C. 154(b), the term of this patent shall be extended for 0 days.

(21) Appl. No.: 08/663,191

(22) PCT Filed: Mar. 22, 1996

(86) PCT No.: PCT/JP96/00762

§ 371 Date: Jun. 11, 1996

§ 102(e) Date: Jun. 11, 1996

(87) PCT Pub. No.: WO96/30506

PCT Pub. Date: Oct. 3, 1996

(30) Foreign Application Priority Data

Mar. 24, 1995 (JP) .................................................. 7-065577

(51) Int. Cl.[7] .......................... G01N 33/53; C07K 16/24; C12N 5/12

(52) U.S. Cl. ........................ 435/7.1; 435/70.21; 435/326; 435/331; 435/336; 435/346; 435/810; 530/350; 530/387.1; 530/387.9; 530/388.1; 530/388.23; 530/388.24; 530/412; 530/413

(58) Field of Search .............................. 424/130.1, 139.1, 424/152.1; 435/7.1, 331; 530/350, 388.1

(56) References Cited

FOREIGN PATENT DOCUMENTS 0 482 623 A2   4/1992   (EP) .
0 555 785 A1   8/1993   (EP) .

OTHER PUBLICATIONS

I. Watanabe et al. J. Biol. Chem. 269:9966–9973 (1994).*
Debets et al. Immunol. Today 15: 455–458 (1994).*
Shing et al. "Betacellulin: A mitogen from pancreatic β cell tumors", Science, vol. 259, No. 5101, pp. 1604–1607, Mar. 1993.
Sasada et al., "Betacellulin: a new growth factor for vascular smooth muscle cells", Nippon Rinsho, 51(12), pp. 3308–3317. (English Abstract) (1993).
Sasada et al., "Cloning and expression of cDNA encoding human betacelluin, a new member of the EGF family", Biochemical and biophysical research communications, vol. 190, No. 3, pp.1173–1179, Feb. 1993.
Watanabe et al., "Recombinant human betacellulin", The Journal of Biological Chemistry, vol. 269, No. 13, pp. 9966–9973, Apr. 1994.

* cited by examiner

*Primary Examiner*—Phillip Gambel
(74) *Attorney, Agent, or Firm*—Wenderoth, Lind & Ponack, L.L.P.

(57) ABSTRACT

Disclosed are an antibody which have a binding activity to human betacellulin protein or a mutein thereof with specificity; especially a monoclonal antibody which does not have cross reactivity with human epidermal growth factor (EGF) and human transforming growth factor a (TGF-α), belongs to the immunoglobulin class of IgG, and, specifically binds to human betacellulin protein to neutralize biological activity thereof; a hybridoma for producing the monoclonal antibody; and a method for producing the monoclonal antibody. Said monoclonal antibody neutralizes biological activity of a human BTC protein, and bind to the protein with high sensitivity and specificity, so that they can be used as a therapeutic agent for diseases such as arterial sclerosis and cancers, and also used as a reagent for assaying the human BTC protein or a mutein thereof and as a diagnostic agent for diabetes or complications thereof.

8 Claims, 20 Drawing Sheets

FIG. 3-1

```
         10         20         30         40         50         60
CAGCGTGGAGGCTCCAAGGACCAAGTCCTGCGCCTCTTTGGCGGGGTGTGTGCAGGAGGA 70         80         90        100        110        120
GGGGGGATAAATAGGAGGCTCCCTCCTCCCGGCGACATTCACGGAGCCGGCCGGCCTCCC 130        140        150        160        170        180
GCCCTGGGTGTTTCCCTGCCTTGTAGCCAGGGTGCCAGCCTGGGAAGTAGTTTCGTTTCC 190        200        210        220        230        240
TTCTGCCTCCGGGATTAGTTTCCAGGCACCCTCTCAGGCGCCCGAGGCCCGGGAAGGGGG 250        260        270        280        290        300
CGAAGAAGGAGGGAGACTTGTCTAGGGGCTGCCCGGCCCGGCAGAGCGGGGTTGATGGAC
                                                         MetAsp
                                                           -31

310        320        330        340        350        360
CGGGCCGCCCGGTGCAGCGGCGCCAGCTCCCTGCCACTGCTCCTGGCCCTTGCCCTGGGT
ArgAlaAlaArgCysSerGlyAlaSerSerLeuProLeuLeuLeuAlaLeuAlaLeuGly 370        380        390        400        410        420
CTAGTGATCCTTCACTGTGTGGTGGCAGATGGGAATTCCACCAGAAGTCCTGAAACTAAT
LeuValIleLeuHisCysValValAlaAspGlyAsnSerThrArgSerProGluThrAsn
         ↑ +1                                                 10

430        440        450        460        470        480
GGCCTCCTCTGTGGAGACCCTGAGGAAAACTGTGCAGCTACCACCACACAATCAAAGCGG
GlyLeuLeuCysGlyAspProGluGluAsnCysAlaAlaThrThrThrGlnSerLysArg
                   20                                       30

490        500        510        520        530        540
AAAGGCCACTTCTCTAGGTGCCCCAAGCAATACAAGCATTACTGCATCAAAGGGAGATGC
LysGlyHisPheSerArgCysProLysGlnTyrLysHisTyrCysIleLysGlyArgCys
                   40                                       50

550        560        570        580        590        600
CGCTTCGTGGTGGCCGAGCAGACGCCCTCCTGTGTCTGTGATGAAGGCTACATTGGAGCA
ArgPheValValAlaGluGlnThrProSerCysValCysAspGluGlyTyrIleGlyAla
                   60                                       70

610        620        630        640        650        660
AGGTGTGAGAGAGTTGACTTGTTTTACCTAAGAGGAGACAGAGGACAGATTCTGGTGATT
ArgCysGluArgValAspLeuPheTyrLeuArgGlyAspArgGlyGlnIleLeuValIle
                   80                                       90

670        680        690        700        710        720
TGTTTGATAGCAGTTATGGTAGTTTTTATTATTTTGGTCATCGGTGTCTGCACATGCTGT
CysLeuIleAlaValMetValValPheIleIleLeuValIleGlyValCysThrCysCys
                  100                                      110
```

FIG. 3 — 2

```
         730       740       750       760       770       780
CACCCTCTTCGGAAACGTCGTAAAAGAAAGAAGAAAGAAGAAGAAATGGAAACTCTGGGT
HisProLeuArgLysArgArgLysArgLysLysLysGluGluGluMetGluThrLeuGly
                            120                           130

790       800       810       820       830       840
AAAGATATAACTCCTATCAATGAAGATATTGAAGAGACAAATATTGCTTAAAAGGCTATG
LysAspIleThrProIleAsnGluAspIleGluGluThrAsnIleAlaEnd
                            140              147

850       860       870       880       890       900
AAGTTACCTCCAGGTTGGTGGCAAGCTGCAAAGTGCCTTGCTCATTTGAAAATGGACAGA 910       920       930       940       950       960
ATGTGTCTCAGGAAAAACAGCTAGTAGACATGAATTTTAAATAATGTATTTACTTTTTAT 970       980       990      1000      1010      1020
TTGCAACTTTAGTTTGTGTTATTATTTTTAATAAGAACATTAATTATATGTATATTGTC 1030      1040      1050      1060      1070      1080
TAGTAATTGGGAAAAAAGCAACTGGTTAGGTAGCAACAACAGAAGGGAAATTTCAATAAC 1090      1100      1110      1120      1130      1140
CTTTCACTTAAGTATTGTCACCAGGATTACTAGTCAAACAAAAAAGAAAAGTAGAAAGGA 1150      1160      1170      1180      1190      1200
GGTTAGGTCTTAGGAATTGAATTAATAATAAAGCTACCATTTATCAAGCATTTACCATGT 1210      1220      1230      1240      1250      1260
GCTAATAAGTTTGAAATATATTATTTCCTTTATTCCTTTCAGCAATCCATGAGATAGCTA

1270
TTATAATCCTC
```

FIG. 14

```
     1   cDNA     M D G N S T R S P E T N G L L C G D P E
         BTC-I    M D G N X T R S P E T N G L L X G D P E 21   cDNA     E N C A A T T Q S K R K G H F S R C P
                                        BTC-II    R K G X F S R X P 41   cDNA     K Q Y K H Y C I K G R C R F V V A E Q T
                  K Q Y K H Y X I — K G — G R F V V A E Q T
```

HUMAN BETACELLULIN-SPECIFIC ANTIBODIES AND USES THEREOF

BACKGROUND OF THE INVENTION

1. Field of the Invention

The present invention relates to an antibody to a human betacellulin (hereinafter also referred to as "BTC") protein or a mutein thereof, a hybridoma, their production and use thereof.

2. Description of the Preferred Embodiments

As to the family of epidermal growth factors, since epidermal growth factor (EGF) was discovered by S. Cohen, *J. Biol. Chem.*, 237, 1555 (1962), *Dev. Biol.*, 12, 394 (1965), various factors have been discovered. These factors are considered to have various functions such as differentiation, maturation, survival, functional retention and proliferation of not only epidermal cells, but also of various cells. Specifically, these factors include transforming growth factor α (TGF-α) [G. J. Todaro and J. E. DeLarco, *Nature*, 264, 26 (1976) and H. Marquardt et al., *Proc. Natl. Acad. Sci. USA*, 80, 4684 (1983)], amphiregulin [M. Shoyab et al., *Science*, 243, 1074 (1989)] and heparin-binding EGF (HB-EGF) [S. Higashiyama et al., *Science*, 251, 936 (1991)], in addition to EGF described above.

Human BTC protein is described in EP-A 0555785, and reported in *Biochem. Biophys. Res. Commun.*, 190, 1173–1179 (1993). BTC protein was discovered as a novel cell growth factor produced by a transgenic mouse-derived pancreatic beta tumor cell [Y. Shing et al., *Science*, 259, 1604 (1993)]. Further, based on the nucleotide sequence of the gene thereof, the human BTC gene was cloned, and the characteristics of BTC protein were studied. As a result, from these studies, the following characteristics were discovered. (1) A precursor molecule having a transmembrane domain is processed at the C-terminus to produce matured type BTC protein, protein. (2) The BTC gene is expressed in the normal mouse kidney, lung, liver and pancreatic beta cells. (3) BTC protein exhibits growth promoting activity on a vascular smooth muscle cell and a retinal pigment epithelial cell. (4) BTC protein acts on an EGF receptor as a ligand [T. Watanabe et al., *J. Biol. Chem.*, 269, 9966 (1994)]. From these, it is conceivable that BTC protein plays an important role in various organs, and abnormal expression thereof possibly induces diseases. Further, these results suggest the possibility that BTC protein contributes to the growth of smooth muscle cells relating to the crisis and progress of arterial sclerosis, and particularly to the possibility that BTC protein is involved in the crisis of diabetic vascular complications such as diabetic arterial sclerosis and diabetic retinitis or in the canceration of cells.

An antibody inhibiting BTC protein activity is considered to be used as one therapeutic agent for diseases in which BTC protein is involved. However, such a report which relates to an antibody to a human BTC Protien has not been presented till now. The assay of the human BTC protein level in the body fluids is also considered as one means for diagnosing the diseases as described above. However, it has not yet been achieved.

As described above, human BTC protein may participate in the crisis and progress of arterial sclerosis, and particularly in the crisis of diabetic vascular complications or the canceration of cells by its abnormal expression (excess expression). Accordingly, inhibition of excess activity of human BTC protein can conceivably treat these diseases. Therefore, the measurement of human BTC protein level in blood makes it possible to diagnose these diseases. In order to assay human BTC protein existing only in slight amounts in the body fluids, an assay with high sensitivity is required.

SUMMARY OF THE INVENTION

In view of the situations described above, the present inventors have prepared antibodies which offer an assay with high sensitivity for a human BTC protein and which are capable of neutralizing human BTC protein activity. As a result of further intensive investigation based thereon, the present inventors have completed the present invention.

In accordance with the present invention, there are provided (1) An antibody which specifically binds to human BTC protein or a mutein thereof;

(2) The antibody according to (1) wherein human BTC protein has an amino acid sequence of SEQ ID NO:1;

(3) The antibody according to (1) or (2) which is a monoclonal antibody;

(4) The antibody according to any one of (1) to (3) which has no cross-reactivity with at least one of human epidermal growth factor, human transforming growth factor a and mouse BTC protein;

(5) A monoclonal antibody which specifically binds to human BTC protein and is capable of neutralizing the biologial activity of said protein, which does not have cross-reactivity with human epidermal growth factor, human transforming growth factor a and mouse BTC protein, and which belongs to the immuno-globulin class of IgG;

(6) The antibody according to anyone of (1) to (5) which recognizes an amino acid sequence of 31st (Arg) to 80th (Tyr) of SEQ ID NO:1;

(7) A cloned hybridoma which is composed of a mammalian spleen cell immunized by human BTC protein or a mutein thereof and a homogenic or heterogenic lymphocyte;

(8) A method of producing the monoclonal antibody of (5), which comprises proliferating the hybridoma according to (7) in a liquid culture medium or in an abdominal cavity of a mammal to form and accumulate the monoclonal antibody and then collecting the monoclonal antibody;

(9) A method of detecting and assaying a human BTC protein or a mutein thereof which comprises contacting the antibody according to anyone of (1) to (6) with a specimen;

(10) A method of diagnosing diabetes or complications thereof which comprises contacting the antibody according to anyone of (1) to (6) with a specimen and assaying a human BTC protein or a mutein thereof in the speciman;

(11) A pharmaceutical composition which comprises an effective amount of the antibody according to anyone of (1) to (6) and a pharmaceutically acceptable carrier, excipient or diluent;

(12) The pharmaceutical composition according to (11) for diagnosing diabetes or complications thereof;

(13) A kit for diagnosing diabetes or complications thereof which comprises an effective amount of the antibody according to anyone of (1) to (6);

(14) A kit for detecting and assaying a human BTC protein or a mutein thereof which comprises an effective amount of the antibody according to anyone of (1) to (6); and

(15) A method of purifying a human BTC protein or a mutein thereof which comprises contacting the antibody according to anyone of (1) to (6) with a crude sample containing the protein or a mutein thereof and isolating it.

BRIEF DESCRIPTION OF THE DRAWINGS

FIGS. 3–1 and 3–2 show a nucleotide sequence of cDNA of BTC-I obtained in Example 4 of EP-A 0555785 (SEQ ID NO:2) and an amino acid sequence deduced therefrom (SEQ ID NO:4);

FIG. 14 shows N-terminal amino acid sequences of BTC-I SEQ ID No.9 and BTC-II SEQ ID No:10 obtained in Reference Example 6 and their correspondence to residues 1–59 of SEQ ID No. 1 (note that the N-terminal of BTC-I and SEQ ID No. 1 start from translation initiation methionine).

DESCRIPTION OF THE PREFERRED EMBODIMENTS

Figure 1:
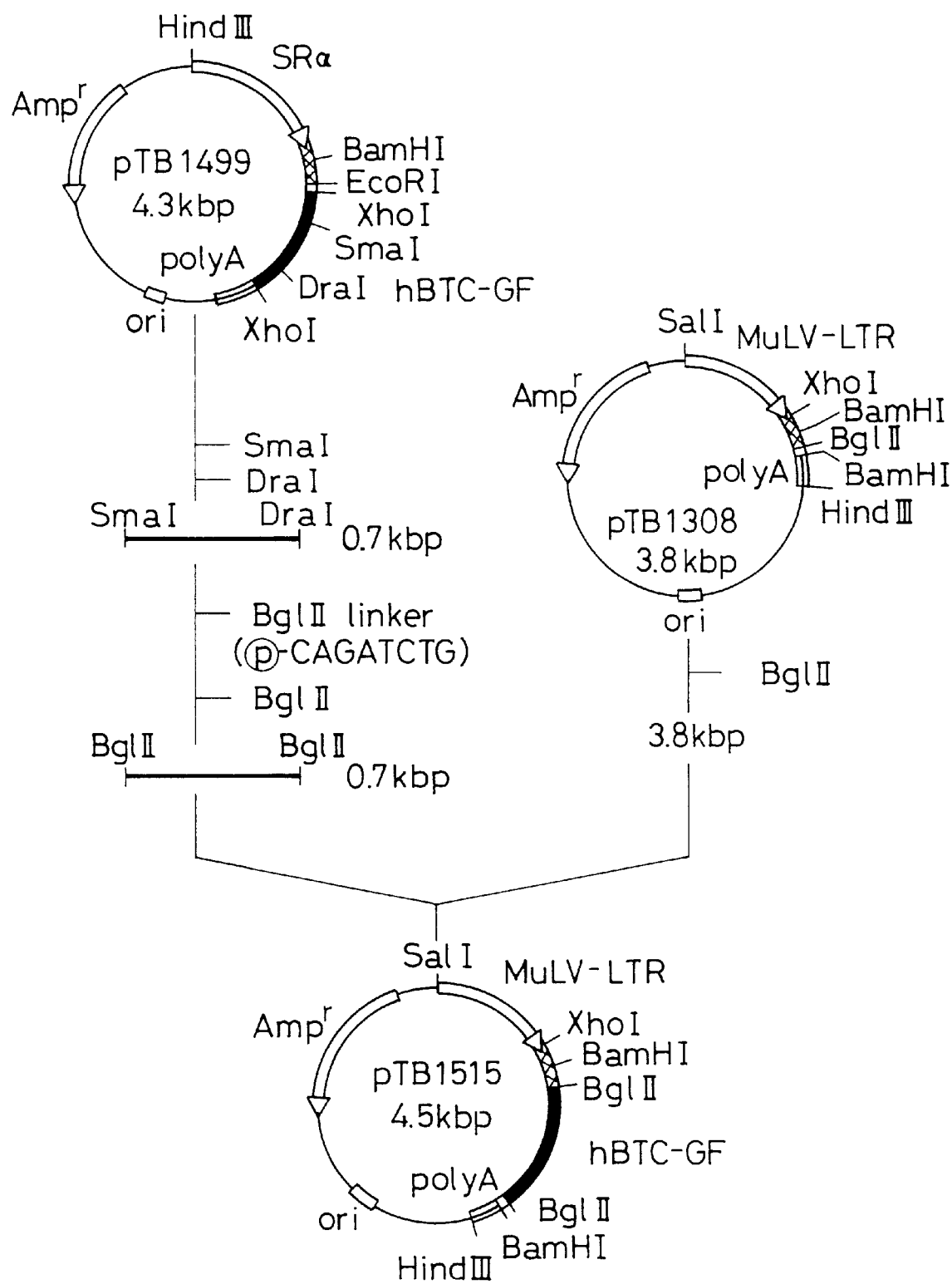
FIG. 1 is a schematic representation showing the construction of plasmid pTB1515.

Human BTC proteins are targets of the antibodies of the present invention and may be any as long as they are human-derived proteins having BTC-like activity, namely cell growth stimulating activity, such as fibroblasts, vascular smooth muscle cells and retinal pigment epithelial cells. They may be natural proteins extracted from various organs such as a liver, a kidney, etc. or recombinant proteins produced by genetic engineering technique.

Examples of the human-derived BTC proteins which can be used include a mature type protein having the amino acid. sequence represented by SEQ ID NO:1 (refer to EP-A 0555785) and a precursor protein having the amino acid sequence represented by SEQ ID NO:4.

These BTC proteins may be simple proteins consisting of amino acids alone or conjugated proteins such as glycoproteins, lipoproteins, hemoproteins, metalloproteins, flavoproteins and phosphoproteins. In the case of glycoproteins, sugar chains include neutral sugars such as D-mannose, D-galactose and L-fructose, amino sugars such as D-glucosamine and D-galactosamine, and sialic acid.

Muteins of the human BTC proteins which can be used include, for example, deletion type muteins in which at least one constituent amino acid is deleted from each of the above-mentioned human BTC proteins, substitution type muteins in which at least one constituent amino acid of each of the BTC proteins is substituted by another amino acid(s), and addition type muteins in which at least one constituent amino acid is added to each of the BTC proteins. The numbers of deleted, substituted or added amino acids may be any as long as the inherent activities of the BTC proteins are not lost. Specifically, there can be used proteins having (1) amino acid sequences in which about 1 to about 40 amino acids are deleted from the amino acid sequence represented by SEQ ID NO: 1 or SEQ ID NO:4, (2) amino acid sequences in which about 1 to about 10 amino acids of the amino acid sequence represented by SEQ ID NO: 1 or SEQ ID NO:4 are substituted by another amino acid(s) or (3) amino acid sequences in which about 1 to about 40 amino acids are added to the amino acid sequence represented by SEQ ID NO: 1 or SEQ ID NO:4.

Of these muteins, deletion type muteins are preferred.

For example, proteins having amino acid sequences in which about 1 to about 40 amino acids are deleted from the N-terminus of the amino acid sequence represented by SEQ ID NO: 1 are preferably used. More specifically, a deletion type mutein of the BTC protein having an amino acid sequence in which 12 or 30 amino acids are deleted from the N-terminus of the amino acid sequence represented by SEQ ID NO: 1 are used [Watanabe et al., *Journal of Biochemistry*, 269, 9966 (1994)].

Other muteins of the BTC proteins may be used as long as the inherent biological activities of the BTC proteins are not lost. Examples of such muteins include muteins in which the N-termini of the BTC proteins are acylated, glycosylated, or chemically modified with polyethylene glycol derivatives.

In particular, in the present invention, human BTC protein having the amino acid sequence of SEQ ID NO:1 (BTC-I) is preferably used as the human BTC protein. In this case, the protein may be a mixture of one further having a methionine residue (Met) at the amino terminus thereof and one having no methionine residue, or may be one having no methionine residue (Met) at the amino terminus and starting with the subsequent aspartic acid residue (Asp).

As the mutein of the BTC protein, there is preferably used a deletion type human BTC mutein (human BTC-II) in which 30 amino acids are deleted from the N-terminus of the amino acid sequence of BTC-I having the amino acid sequence represented by SEQ ID NO: 1.

Of the BTC proteins and the muteins thereof used in the present invention, the human BTC protein having the amino acid sequence represented by SEQ ID NO: 1 and the deletion type human BTC mutein having the amino acid sequence in which 12 or 30 amino acids are deleted from the N-terminus of the amino acid sequence represented by SEQ ID NO: 1 are known. The other BTC proteins and the muteins thereof can be prepared by methods known in the art or methods based thereon.

Methods of preparing the antibodies of the present invention are shown as follows.

The monoclonal antibodies of the present invention which specifically bind to a human BTC protein or a mutein thereof and neutralize biological activity thereof are prepared by immunizing mammals with a BTC protein or a mutein thereof. When the mammals are immunized with a human BTC protein or a mutein thereof described above, the mammals used for immunization include experimental animals such as sheep, goat, rabbits, guinea pigs, rats and mice. In order to obtain the monoclonal antibodies, rats and mice are preferred, and mice are particularly suitable. When mice are immunized, for example, any of the subcutaneous, intraperitoneal, intravenous, intramuscular and intracutaneous routes is available. Mainly, subcutaneous, intraperitoneal and intravenous injections are preferred, and the subcutaneous injection is particularly preferred. The immunizing interval and the immunizing dose are widely changeable, and various methods are available. For example, immunization is generally carried out about 2 to about 6 times at intervals of about 2 weeks and spleen cells removed about 1 to about 5 days, preferably about 2 to about 4 days after the final immunization. The immunizing dose is preferably about 0.1 µg or more, and more preferably about 10 to about 300 µg per mouse, as the peptide amount per one immunization. Further, it is preferred to carry out a cell fusion using the spleen cells after confirmation of an increase in antibody titer in the blood by collecting partial blood before removal of the spleens.

The thus-prepared spleen cells are fused with lymphoid cells. For example, the spleen cells removed from the mice are fused with lymphoid cells such as homogeneous or heterogeneous (preferably homogeneous) myeloma cells, for example, P3-X63-Ag 8UI [Ichimori et al., *J. Immun. Method*, 80, 55 (1985)], having characteristics useful as selection marker such as hypoxanthine-guanine-phosphoribosyl transferase deficient (HGPRT$^-$) or thymidine kinase deficient (TK$^-$). The hybridoma cells can be produced by fusion, for example, in accordance with the method of Köhler and Milstein [*Nature*, 256, 495 (1975)]. Namely, for example, the myeloma cells and the spleen cells are suspended in a ratio of about 1:5 in a 1:1 mixed medium of Iscove medium and Ham F-12 medium (hereinafter referred to as IH medium), and a fusogen such as Sendai virus or polyethylene glycol (PEG) is added thereto. It is of course possible to add another fusogen such as dimethyl sulfoxide (DMSO). The molecular weight of PEG is usually about 1,000 to about 6,000, time for the fusion is from about 0.5 to about 30 minutes, and the concentration is from about 10 to about 80%. As a preferred example, fusion is conducted in a concentration of about 35 to about 55% for about 4 to about 10 minutes using PEG 6,000, which results in efficient fusion. The fused cells can be selectively proliferated using hypoxanthine-aminopterin-thymidine medium (HAT medium) [*Nature*, 256, 495 (1975)].

The culture supernatant of the proliferated cells can be screened whether a desired antibody has been produced or not. The screening of the antibody titer can be carried out in the following manner. In this case, first, the presence or absence of the antibody produced by peptide immunization can be examined by known assays such as radio-immunoassays (RIAs) or enzyme immunoassays (EIAs). For these methods, various modified assays are also available. As a preferred example of the assays, a method using the EIA is hereinafter described. A rabbit anti-mouse immunoglobulin antibody is coupled to a carrier such as cellulose beads according to conventional methods, and then a culture supernatant or mouse serum to be assayed is added thereto, followed by reaction at a room temperature (about 4 to about 40° C. in this specification, hereinafter the same) for a defined time. After the reaction product is thoroughly washed, an enzyme-labeled peptide obtained by chemically conjugating the enzyme with the peptide and purifying the resulting product is added thereto and the reaction is carried out at a room temperature for a defined time. After the reaction product is thoroughly washed, an enzyme substrate is added thereto, followed by reaction at a room temperature for a defined time. Then, the absorbance or fluorescence of the product can be measured.

The cells in wells which show cell proliferation in a selective medium and antibody activity upon the peptide used for immunization is preferably cloned by a limiting dilution method. The supernatant of the cloned cells is screened for a high antibody titer, proliferating cells in a well which shows higher antibody titer, thereby obtaining monoclonal antibody-producing hybridoma clones showing reactivity with the immunized peptide.

The hybridoma cells thus cloned are proliferated, for example, in a liquid medium. Specifically, for example, the hybridoma cells are cultivated in a known liquid medium such as a medium comprising RPMI-1640 [G. E. Moore et al., *J. Am. Med. Assoc.*, 199, 549 (1967)] with about 0.1–40% bovine serum for about 2 to about 10 days, preferably for about 3 to about 5 days, whereby the monoclonal antibody can be obtained from the cultivate solution. The desired antibody can also be obtained by intraperitoneally inoculating mammals with the above-mentioned monoclonal antibody-producing hybridoma cells to proliferate the hybridoma cells, and then collecting the ascites. For example, in the case of mice, about $1\times10^4$ to about $1\times10^7$ cells, preferably about $5\times10^5$ to about $2\times10^6$ cells of the above-mentioned monoclonal antibody-producing hybridoma are intraperitoneally inoculated into mice such as BALB/c previously inoculated with mineral oil, etc., and the ascites is collected after about 7 to about 20 days, preferably after about 10 to about 14 days. From the antibodies produced and accumulated in the ascites, the desired BTC monoclonal antibody can be easily isolated as pure immunoglobulin by ammonium sulfate fractionation, DEAE-cellulose column chromatography, etc.

The polyclonal antibodies of the present invention can be prepared by methods known in the art or methods based thereon.

Immunogens used herein include, for example, the human BTC polypeptides, the muteins thereof and polypeptides having parts of the amino acid sequence from the 31st (Arg) to the 80th (Thr) of the amino acid sequence represented by SEQ ID NO: 1. The polypeptides used as an antigen are preferably the polypeptides having more than 10 amino acid residues. For example, the polypeptide having 15 amino acid residues from 66th to 88th of the amino acid sequence represented by SEQ ID NO:1 can be used as an antigen. The polypeptides can be prepared by peptide synthesis methods known in the art or methods based thereon, and either the solid phase synthesis methods or the liquid phase synthesis methods may be employed.

The polyclonal antibodies can be prepared by producing conjugates of the immunogens and carrier polypeptides, immunizing mammals with the conjugates in a manner similar to that of the above-mentioned monoclonal antibodies, collecting products containing antibodies of BTC or muteins thereof from the immunized mammals, and isolating and purifying the antibodies.

As to the conjugates of the immunogens and the carrier proteins used for immunizing the mammals, the kinds of carrier proteins and the mixing ratios of the carrier proteins and the haptens may be any, as long as the antibodies can be efficiently obtained to the haptens coupled to the carrier proteins for immunization. For example, bovine serum albumin, bovine thyroglobulin or hemocyanin is coupled to the hapten in a weight ratio of about 0.1 to about 20:1, preferably about 1 to about 5:1.

In coupling of the haptens and the carrier proteins, various coupling agents can be used. Examples of the coupling agents include glutaraldehyde, carbodiimide reagents, maleimide active ester reagents and active ester reagents having thiol or dithiopyridyl groups.

The condensate is given to a mammal at a site where an antibody may be produced by administration of the condensate, alone or together with a carrier and/or a diluent. In order to enhance antibody production ability, Freund's complete adjuvant or Freund's incomplete adjuvant may be given. The condensate is usually given once for every 2 to 6 weeks, totally about 3 to about 10 times. The mammals used for immunization include monkeys, rabbits, dogs, guinea pigs, mice, rats, sheep and goat.

The antibodies are collected, for example, from the blood or the ascites of the immunized mammals, and preferably from the blood thereof.

The anti-BTC antibody titer in the antisera can be assayed in the same manner as with the above-mentioned assay of the antibody titer in the hybridoma cultivate supernatants. Isolation and purification of the antibodies are performed according to the isolation and purification methods of immunoglobulins similarly to those of the above-mentioned monoclonal antibodies.

The antibodies of the present invention bind to various types of human BTC proteins or muteins thereof described above with high sensitivity and specificity.

The antibodies of the present invention which further have the following characteristics in addition to the characteristics described above are preferred.

a) They do not neutralize biological activity of mouse BTC protein, but neutralize biological activity of human BTC.

b) They do not have immune cross-reactivity with human TGF-α and human EGF.

c) They belong to the immunoglobulin class of $IgG_1$ subclass, and have a molecular weight of 140,000 to 160,000.

d) They recognize specifically the amino acid sequence from 31st (Arg) to 80th (Tyr) of SEQ ID NO:1 (50-amino acid sequence).

Examples of the mouse BTC proteins used include a maturation type mouse BTC protein having the amino acid sequence represented by SEQ ID NO: 3 [Y. Shing et al., *Science*, 259, 1604 (1993)]. The amino acid sequence of this mature type mouse BTC protein has about 80% homology with that of the mature type human BTC protein having the amino acid sequence represented by SEQ ID NO: 1.

However, the preferred antibodies of the present invention, especially the monoclonal antibodies of the present invention, have the very unique characteristics that they do not bind to the mouse BTC proteins, but specifically bind to the human BTC proteins.

For example, the human BTC monoclonal antibodies produced from the hybridoma obtained in the example described below have the above-mentioned characteristics (a) to (d).

The antibodies of the present invention may be any, as long as they specifically bind to human BTC and neutralize biological activity thereof. The biological activities of the human BTC protein neutralized by the antibody of the present invention are, for example, cell growth stimulating activity such as fibroblasts, vascular smooth muscle cells or retinal pigment epithelial cells. Examples of the monoclonal antibodies include antibodies 1A1, 2B2 and 5E5 produced by anti-human BTC monoclonal antibody-producing hybridomas 1A1, 2B2 and 5E5 obtained in the example 2 described below.

Examples of the polyclonal antibodies include one obtained in the example 10 described below.

For example, the monoclonal antibodies obtained in the examples described below inhibit a DNA synthesis induction of resting mouse 3T3 cells in the presence of 1 ng/ml of human BTC by addition of 1 μg/ml of the antibodies. Further, 10 pg/ml of a human BTC protein can be detected by a sandwich ELISA method using the monoclonal antibody and a biotinated antibody.

The antibodies of the present invention binding to a human BTC protein or a mutein thereof can be also used for detection and determination of a human BTC protein or a mutein thereof.

Detection and determination of a human BTC protein or a mutein thereof using the antibodies of the present invention can be performed, for example, by the immunochemical assay of measuring the human BTC protein using an human BTC antibody of the present invention bound to a carrier and a conjugate in which a labeling agent is directly bound to an anti-BTC antibody different from the former antibody in the antigen recognition site. The enzyme immunoassay is preferably employed among others.

The antibodies of the present invention are used as both the antibody held on the carrier and the antibody different from the above-mentioned antibody in the antigen recognition site used in the above-mentioned assay, and the monoclonal antibodies are preferably used. Preferred examples of the monoclonal antibodies include antibodies 1A1, 2B2 and 5E5 prepared in the example described below, and they may be appropriately selected.

Examples of the carriers to which the antibodies are bound in the above-mentioned assays include gel particles for example, agarose gels such as Sepharose 4B and Sepharose 6B (Pharmacia Fine Chemical, Sweden), dextran gels such as Sephadex G-75, Sephadex G-100 and Sephadex G-200 (Pharmacia Fine Chemical, Sweden) and polyacrylamide gels such as Biogel P-30, Biogel P-60 and Biogel P-100 (Bio RAD Laboratories, U.S.A.); cellulose particles, for example, Avicel (Asahi Chemical Industry, Japan) and ion exchange cellulose such as diethylaminoethyl cellulose and carboxymethyl cellulose; physical adsorbents, for example, glass such as glass balls, glass rods and aminoalkyl glass rods, silicone pieces, styrenic resins such as polystyrene balls and polystyrene particles, and plates for immunoassay (for example, Nunc, Denmark); and ion exchange resins, for example, weakly acidic cation exchange resins such as Amberlite IRC-50 (Rohm & Haas, U.S.A.) and Zeocurve 226 (Permutit, West Germany), and weakly alkalic anion exchange resins such as Amberlite IR-4B and Dowex (Dow Chemical, U.S.A.).

In order to bind the antibody on the carrier, conventional methods can be used. Examples of such methods include the cyanogen bromide method and the glutaraldehyde method which are described in *Metabolism*, 8, 696 (1971). As a simpler method, the antibody may be physically adsorbed on the surface of the carrier.

Examples of the labeling agents in the labeling agent-bound antibody conjugates include radioisotopes, enzymes, fluorescent substances and luminous substances, and enzymes are preferably used. Enzymes which are stable and high in specific activity are preferred, and peroxidases, alkaline phosphatases, β-D-galactosidases, glucose oxidases and the like can be used. Peroxidases are preferred among others, and peroxidases of various origins can be used. Examples thereof include peroxidases derived from horseradishes, pineapples, figs, sweet potatoes, broad beans and corn. Horseradish peroxidase (HRP) extracted from horseradishes is preferred among others.

In binding the peroxidase to the antibody, the peroxidase into which a maleimido group is preliminarily introduced is conveniently used to utilize the thiol group of Fab' as an antibody molecule.

When the maleimido group is introduced into the peroxidase, the maleimido group can be introduced through an amino group of the peroxidase. For this purpose, N-succinimidyl-maleimide-carboxylate derivatives can be used, and N-(γ-maleimidobutyloxy)succinimide (hereinafter also referred to as "GMBS") is preferably used. A certain group may therefore intervene between the maleimide group and the peroxidase.

GMBS reacts with the peroxidase in a buffer having a pH of about 6 to about 8 at about 10 to about 50° C. for about 10 minutes to about 24 hours. The buffer solutions include, for example, 0.1 M phosphate buffer (pH 7.0). The maleimidated peroxidase thus prepared can be purified, for example, by gel chromatography. Examples of carriers used in the gel chromatography include Sephadex G-25 (Pharmacia Fine Chemical, Sweden) and Biogel P-2 (Bio RAD Laboratories, U.S.A.).

The maleimidated peroxidase can be reacted with the antibody molecule in a buffer at about 0 to about 40° C. for about 1 to about 40 hours. Examples of the buffers include 0.1 M phosphate buffer (pH 6.0) containing 5 mM sodium ethylenediaminetetraacetate. The peroxidase-labeled antibody thus prepared can be purified, for example, by gel chromatography. Examples of carriers used in the gel chromatography include Sephadex G-25 (Pharmacia Fine Chemical, Sweden) and Biogel P-2 (Bio RAD Laboratories, U.S.A.).

Further, a thiol group may be introduced into the peroxidase to react with the maleimidated antibody molecule.

Enzymes other than the peroxidases can also be directly bound to antibodies based on the methods used for binding the peroxidases. Known methods which achieve such binding include, for example, the glutaraldehyde method, the periodic acid method and the water-soluble carbodiimide method.

Specimens to be tested in an assay system (detection and determination of human BTC protein) used in the present invention include the body fluids such as the urine, the serum, the plasma and the cerebrospinal fluid, extract of animal cells, and culture supernatants thereof.

As an example of assays (detection and determination of human BTC protein) used in the present invention, a case is hereinafter described in detail in which a peroxidase is used as the labeling agent, but the present invention is not limited thereto.

(1) First, a specimen containing a human BTC protein to be assayed is added to an antibody bound to a carrier to conduct the antigen-antibody reaction, and then the conjugate of the peroxidase with the anti-human BTC protein antibody obtained above is added thereto to allow them to react with each other.

(2) A substrate of the peroxidase is added to the reaction product obtained in (1), and then the absorbance or the fluorescent intensity of the resulting substance is measured, thereby detecting enzyme activity of the above-mentioned reaction product.

(3) A standard solution containing a known amount of the human BTC protein is previously subjected to the procedures of the above (1) and (2) to prepare a standard curve showing the relation between the amount of the human BTC protein and the absorbance or the fluorescent intensity thereof.

(4) The absorbance or the fluorescent intensity obtained for the specimen (sample to be tested) containing an unknown amount of the human BTC protein is applied to the standard curve to determine the amount of the human BTC protein contained in the specimen.

This method of detecting and assaying a human BTC protein or a mutein thereof can be used for a diagnosis of diabetes or complications thereof.

The antibodies of the present invention can be used for a purification of a human BTC protein or a mutein thereof in a crude sample.

For the purification of the human BTC protein, the purified antibody of the present invention is coupled with an appropriate carrier such as activated agarose gel beads according to conventional methods, followed by packing in a column. Then, a sample containing the crude human BTC protein, such as a culture supernatant or a fluid of disrupted cells, is loaded onto the antibody column to allow the sample to be adsorbed thereby, followed by washing. Thereafter, the column is eluted with a chaotropic reagent such as potassium thiocyanate (KSCN) or under such acidic conditions that human BTC is not inactivated. Thus, the human BTC protein can be efficiently purified.

The antibody column using the antibodies of the present invention can be prepared by coupling the monoclonal antibody of the present invention with an appropriate carrier, said antibody being, for example, purified from ascites or other fluids inoculated with hybridoma cells, in the following manner.

Any carrier may be used as long as the human BTC protein is specifically efficiently adsorbed thereby after coupling and suitable elution is thereafter possible. Examples of the carriers include agarose, cellulose and acrylamide polymers. As an example, agarose gel beads in which a primary amine of a protein is activated so as to be easily bindable, such as Affi-Gel 10 (Bio RAD), are conveniently used according to the following method. The antibody is reacted with Affi-Gel 10 in a buffer such as a bicarbonate solution having a concentration of about 0.001 to about 1 M, preferably about 0.1 M. The reaction can be conducted at about 0 to about 20° C. at various pH values for about 10 minutes to about 24 hours, and preferably at about 4° C. at a pH of about 3 to about 10 for about 4 hours. With respect to the mixing ratio of the antibody to Affi-Gel 10, the amount of the antibody which becomes bound to Affi-Gel 10 increases as the amount of the antibody mixed therewith increases, until the ratio reaches about 50 mg of antibody per 1 ml of Affi-Gel 10. Hence, any ratio can be employed within this range. However, about 10 to about 30 mg of the antibody is conveniently used, considering the binding efficiency and the purification efficiency in affinity column chromatography. The antibody-carrier conjugate thus formed is thoroughly washed with the buffer used in the reaction. Then, residual unreacted active groups are blocked by allowing the washed conjugate to stand for several days, or by adding a compound containing a primary amine such as ethanolamine-hydrochloric acid or glycine thereto to a final concentration of about 0.05 to about 0.10 M, followed by reaction at about 4° C. for about 1 to about 4 hours, or by reacting a protein such as 1–5% bovine serum albumin (BSA) therewith at 4° C. overnight. The conjugate thus treated is packed in an appropriate column to form the antibody column.

In purification with the above-mentioned antibody column, for example, a human BTC protein-containing sample is dissolved in a buffer having a neutral pH such as phosphate buffer or Tris-hydrochloric acid buffer, and adsorbed by the antibody column. Then, the column is washed with the same buffer, followed by elution of the human BTC protein. Eluents which can be used include slightly acidic solutions such as acetic acid solutions, solutions containing polyethylene glycol, solutions containing peptides more easily bindable with the antibody than the sample, high concentration salt solutions and combined solutions thereof. Solutions which do not so accelerate decomposition of the human BTC protein are preferred.

Column eluates are neutralized with buffers by conventional methods. The above-mentioned purification procedure can be repeated if necessary.

Thus, the substantially pure human BTC protein substantially free from pyrogens and endotoxins is obtained. The substantially pure human BTC protein of the present invention contains the human BTC protein at a concentration of about 90% (w/w) or more, and preferably about 95% (w/w) or more.

The antibodies of the present invention bind to a human BTC protein or a mutein thereof with high sensitivity. Accordingly, they are very useful as reagents for assaying (detecting or determination) a human BTC protein or a mutein thereof or as reagents for purifying human BTC protein or a mutein thereof.

An abnormal expression of human BTC protein or a mutein thereof may cause diabetes or complications thereof. In these cases, the diseases can be foreseen by assaying the amount of human BTC protein. The sensitivity of the determination method is required to be as high as possible, because the amount of human BTC produced in vivo is very slight. According to the assays using the monoclonal antibodies of the present invention, the human BTC proteins can be measured down to 10 pg/ml, for example, as shown in Example 8 described below. This is very epochal in that in vivo human BTC existing only in very slight amounts can be assayed. Diseases such as arterial sclerosis and acute tumors are considered as diseases induced by excess production of human BTC.

Accordingly, a diagnosis of diabetes or complications thereof can be conducted by using the antibody of the present invention. Diagnosis can be performed, for example, by the immunochemical assay of measuring the humanl BTC protein using an human BTC antibody bound to a carrier and a conjugate in which a labeling agent is directly boundL to an anti-GAF antibody different from the former antibody in the antigen recognition site. The enzyme immunoassay is preferably employed among others.

The antibodies of the present invention are used as both the antibody held on the carrier and the antibody different from the above-mentioned antibody in the antigen recognition site used in the above-mentioned assay, and the monoclonal antibodies are preferably used. Preferred examples of the monoclonal antibodies include antibodies 1A1, 2B2 and 5E5 prepared in the example described below, and they may be appropriately selected.

Carriers and labelling agents used in the detection and assay can also be used for the diagnosis. Examples of a diagnostic agent comprising the antibodies of the present invention include a combination of peroxidase-bound 5E5 antibody and 1A1 antibody bound to beads, and examples of a diagnosis kit include a combination of peroxidase-bound 5E5 antibody and 1A1 antibody bound to beads and a peroxidase substrate. By the diagnostic agent or the diagnosis kit, a human BTC protein can be assayed and accordingly diabetes or complications thereof be diagnosed.

As described above, the antibodies of the present invention have strong neutralizing activity, and therefore remove excess human BTC protein in vivo to neutralize activity of human BTC protein. For the diseases which might be induced by excess activity of human BTC protein, the antibodies can be given to humans as therapeutic agents.

The antibodies of the present invention are low in toxicity.

While the dosage of the antibodies of the present invention when administered to a patient varies with age, sex of the patient or state of disease, it ranges from about 100 μg/kg to about 10 mg/kg daily.

When the antibodies of the present invention are administered, the antibodies themselves or mixtures thereof with pharmaceutically acceptable carriers, excipients and diluents (for example, water and physiological saline) can be given parenterally in a formulation such as an injection.

Further, when parenteral preparations such as injections are prepared, isotonic agents (for example, glucose, D-sorbitol, D-mannitol and sodium chloride), preservatives (for example, benzyl alcohol, chlorobutanol, methyl p-hydroxybenzoate and propyl p-hydroxybenzoate), buffers (for example, phosphate buffer and sodium acetate buffer), etc. can be appropriately added.

When nucleotides, amino acids and so on are indicated by abbreviations in the specification and drawings, the abbreviations adopted by the IUPAC-IUB Commission on Biochemical Nomenclature or commonly used in the art are employed. For example, the following abbreviations are used. When the amino acids are capable of existing as optical isomers, it is understood that the L-forms are represented unless otherwise specified.

DNA: Deoxyribonucleic acid
A: Adenine
C: Cytosine
G: Guanine
T: Thymine
Ala: Alanine
Arg: Arginine
Asn: Asparagine
Asp: Aspartic acid
Cys: Cysteine
Gln: Glutamine
Glu: Glutamic acid
Gly: Glycine
His: Histidine
Ile: Isoleucine
Leu: Leucine
Lys: Lysine Met: Methionine
Phe: Phenylalanine
Pro: Proline
Ser: Serine
Thr: Threonine
Trp: Tryptophan
Tyr: Tyrosine
Val: Valine The present invention will be described in more detail through Reference Examples and Examples shown below. It is understood of course that they are not intended to limit the scope of the invention.

Transformant cell *E. coli* MM294(DE3)/pTB1516 obtained in Reference Example 3 described below was deposited with the National Institute of Bioscience and Human-technology (NIBH) [formerly the Fermentation Research Institute (FRI)], Agency of Industrial Science and Technology, the Ministry of International Trade and Industry, of 1–3, Higashi 1 chome, Tsukuba-shi Ibaraki-ken 305 Japan, under the accession number FERM BP-3836 on Apr. 21, 1992, and with the Institute for Fermentation (IFO) of 17–85, Juso-honmachi 2-chome, Yodogawa-ku, Osaka 532 Japan, under the accession number IFO 15282 on Apr. 16, 1992.

Transformant A9/1515-14 obtained in Reference Example 4 described below was deposited with the IFO of 17–85, Juso-honmachi 2-chome, Yodogawa-ku, Osaka 532 Japan, under the accession number IFO 50389 on Dec. 28, 1992, and with the NIBH of 1–3, Higashi 1 chome, Tsukuba-shi Ibaraki-ken 305 Japan under the accession number FERM BP-4159 on Jan. 13, 1993.

Mouse 1A1 cell, 2B2 cell and 5E5 cell obtained in Example 2 described below were deposited with the IFO of 17–85, Juso-honmachi 2-chome, Yodogawa-ku, Osaka 532 Japan, under the accession numbers IFO 50437, 50438 and 50439 on Feb. 15, 1994, and with the NIBH of 1–3, Higashi 1 chome, Tsukuba-shi Ibaraki-ken 305 Japan under accession numbers FERM P-14847, FERM P-14848 and FERM P-14849 on Mar. 23, 1995 which were transferred to international deposites under accession numbers FERM BP-5393, FERM BP-5394 and FERM BP-5395 on Feb. 13, 1996.

REFERENCE EXAMPLE 1

Construction of Human BTC cDNA Expression Plasmid for Mammalian Cells

Figure 2:
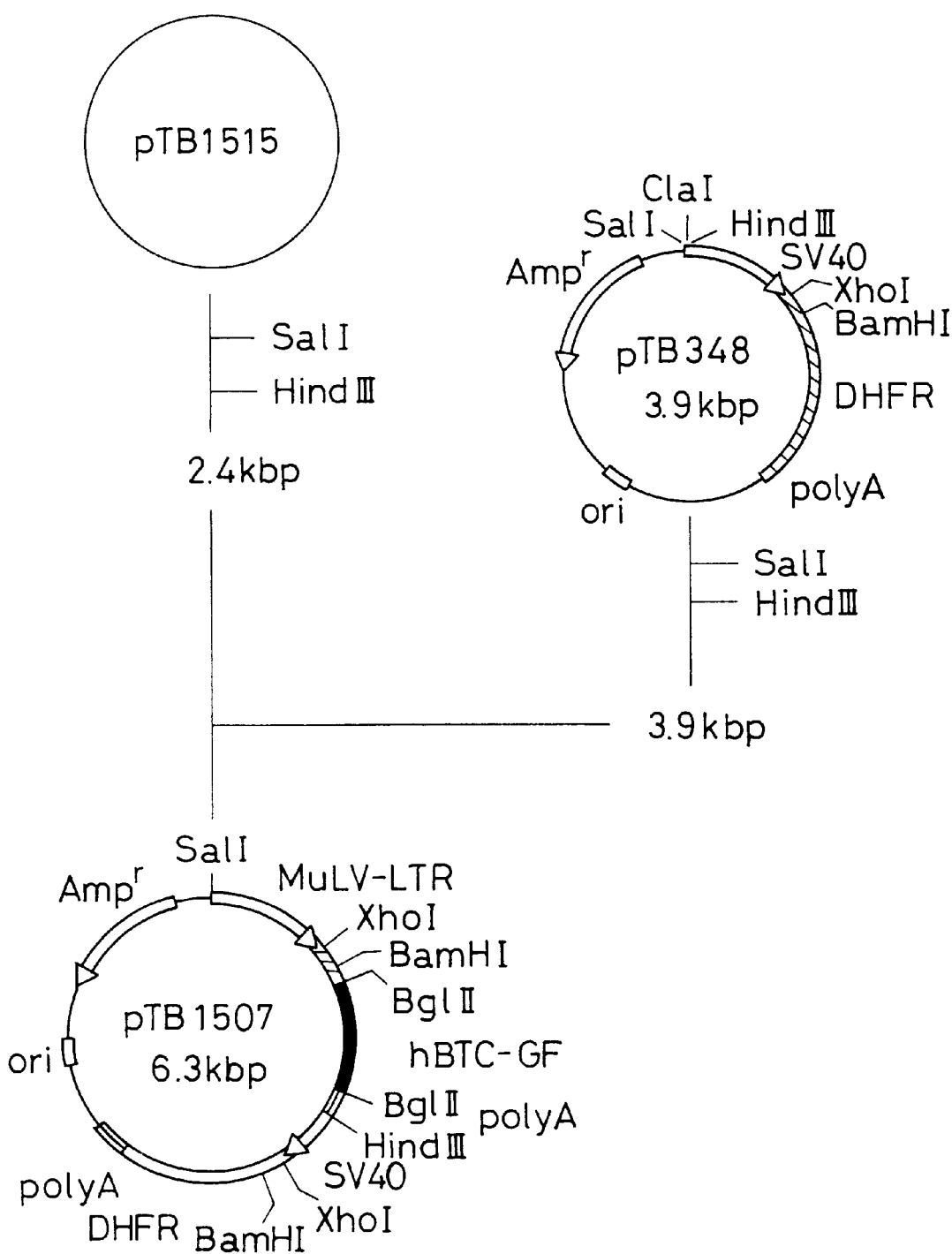
FIG. 2 is a schematic representation showing the construction of plasmid pTB1507.

A 0.7-Kb SmaI-DraI fragment containing cDNA coding for human BTC protein (human BTC cDNA) was isolated from plasmid pTB1499 (refer to Example 4 of EP-A 0555785) [*Biochem. Biophys. Res. Commun.*, 190, 1173 (1993)]. BglII linkers were ligated with this fragment at the flush ends thereof by use of T4 DNA ligase. After digestion with BglII, a 0.7-Kb fragment containing human BTC cDNA was inserted into the BglII site of expression plasmid pTB1308 prepared from pTB399 [*Cell Structure Function*, 12, 205 (1987)] by removing an IL-2 cDNA region, by ligation using T4 DNA ligase (FIG. 1). Plasmid pTB1515 thus produced was cleaved with SalI and HindIII. A 2.4-Kb fragment containing MuLV LTR and human BTC cDNA was isolated and introduced between the SalI and HindIII sites of pTB348 [*Cell Structure Function*, 12, 205 (1987)] having an SV40 early region promoter and hamster DHFR cDNA. The resulting plasmid was named pTB1507 (FIG. 2).

REFERENCE EXAMPLE 2

Construction of Human BTC cDNA Expression Plasmid for *E. coli*

A 0.6-Kb EcoRI-BamHI fragment coding for a human BTC precursor (1–147 amino acid residues) was isolated from plasmid pTB1515 (Reference Example 1). A synthetic adaptor having an ATG translation initiation codon (a: 5' TATGGATGGG 3' (SEQ ID No. 5); b: 5' AATTCCCATCCA 3'(SEQ ID No. 6)) was ligated with the above-mentioned 0.6-Kb fragment at the EcoRI site thereof. Then, the resulting 0.6-Kb NdeI-BamHI fragment was inserted into plasmid pET-3c containing a T7 promoter [*Gene*, 56, 125 (1987)] to construct plasmid pTB1505.

Figure 4:
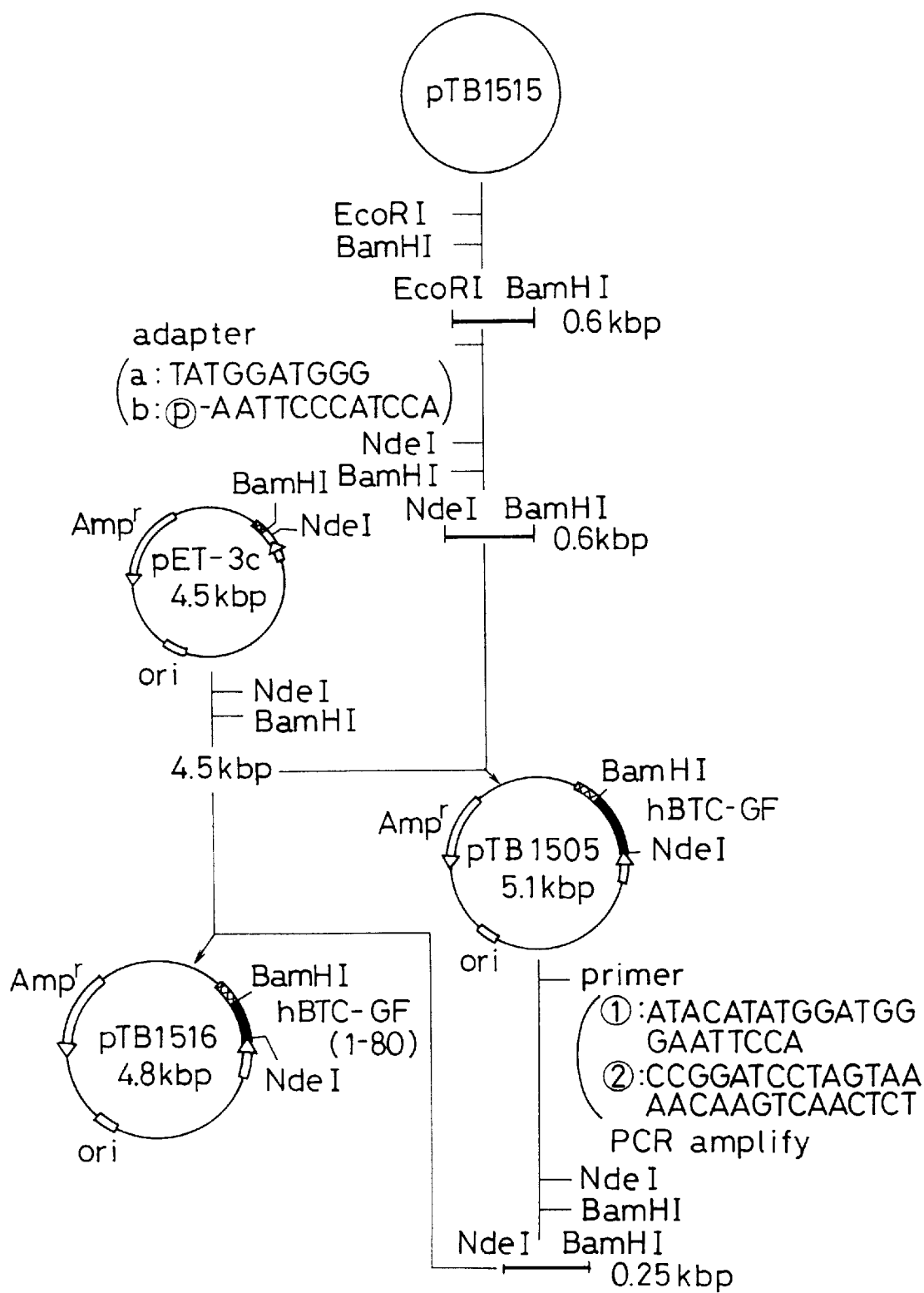
FIG. 4 is a schematic representation showing the construction of plasmid pTB1516.

In order to obtain a DNA fragment coding for 80 amino acid residues [from 1 (Asp) to 80 (Tyr) in FIG. 3] of human BTC protein, PCR was conducted using plasmid pTB1505 as a template and two oligonucleotides (1: 5' ATACATATG-GATGGGAATTCCA 3' (SEQ ID No. 7) and 2: 5' CCG-GATCCTAGTAAAACAAGTCAACTCT 3' (SEQ ID No. 8)) as primers. The product was digested with NdeI and BamHI, and fractionated by 2.0% agarose gel electrophoresis, thereby isolating a desired 0.25-Kb DNA fragment. The 0.25-Kb NdeI-BamHI fragment was inserted downstream from the T7 promoter of pET-3c by ligation through T4 DNA ligase to obtain plasmid pTB1516 (FIG. 4).

REFERENCE EXAMPLE 3

Expression of Human BTC cDNA in *E. coli*

*E. coli* MM294 was lysogenized with lambda phage (study supra) recombinated with an RNA polymerase gene of T7 phage. Then, plasmid pLysS was introduced into *E. coli* MM294(DE3) to obtain *E. coli* MM294(DE3)/pLysS. Plasmid pTB1516 was introduced into this strain, thereby obtaining *E. coli* MM294(DE3)/pLysS, pTB1516. The resulting transformant cells were cultivated in 20 ml of L-broth containing 100 μg/ml ampicillin and 10 μg/ml chloramphenicol at 37° C. When the Klett value was about 180, isopropyl-β-D-thiogalactoside (IPTG) was added to the medium to give a final concentration of 0.4 mM, and cultivation was continued for 4 hours. The resulting cells were collected, and suspended in 0.5 ml of a buffer containing 20 mM Tris-HCl (pH 7.4), 10 mM EDTA, 0.5 M NaCl, 10% sucrose and 0.25 mM PMSF, followed by addition of egg white lysozyme to this suspension at a concentration of 0.5 mg/ml. After placed in an ice bath for 1 hour, the mixed solution was cultivated at 37° C. for 5 minutes, and centrifuged in a Sorvall centrifuge at 15,000 rpm at 4° C. for 30 minutes to obtain a supernatant.

For this cell extract, DNA synthesis induction activity was assayed by the uptake of $^3$H-thymidine into quiescent Balb/c 3T3 clone A31-714-4 cells [*Int. J. Cancer*, 12, 463 (1973)] according to the method described in *Mol. Cell. Biol.*, 8, 588 (1988). Results thereof are shown in Table 1.

In the measurement of human BTC protein biological activity, the DNA synthesis induction activity assay is usually used [T. Watanabe et al., *J. Biol. Chem.*, 269 9966 (1994); EP-A 0555785].

TABLE 1

| Transduced DNA or control | Sample dilution | $^3$H-thymidine uptake (cpm) |
| --- | --- | --- |
| *E. coli* MM294(DE3) /pLysS, pTB1516 | 1/78125 1/390625 | 20,232 13,169 |

TABLE 1-continued

| Transduced DNA or control | Sample dilution | $^3$H-thymidine uptake (cpm) |
|---|---|---|
| E. coli MM294(DE3) /pLysS, pET:3c | 1/3125 | 805 592 |

REFERENCE EXAMPLE 4
Establishment of human BTC-Producing A9 Cell Line

Mouse A9 cells (ATCC CCL 1.4) were co-transfected with human BTC cDNA-containing plasmid pTB1515 (Reference Example 1) and human HPRT gene-containing expression plasmid p4aA8 [D. J. Jolly et al., *Proc. Natl. Acad. Sci. USA*, 80, 477 (1983)] by the calcium phosphate method. The resulting cells were proliferated in DMEM supplemented with 10% fetal calf serum for 2 days, followed by cultivation in HAT medium [J. W. Littlefield, *Science*, 145, 709 (1964)] for selection. HPRT+ cells were proliferated in HAT medium, and clones were isolated by limiting dilution method. Cells ($10^5$ cells) of each clone were plated in each well of a 24-well plate, and cultivated in a growth medium for 2 days, followed by cultivation in 0.5 ml of DMEM containing 0.5% fetal calf serum for 2 days. The human BTC level at which $10^6$ cells were secreted in the medium was examined by DNA synthesis induction activity on the mouse 3T3 cells described in Reference Example 3. Results of several clones are shown in Table 2.

TABLE 2

| Clone | Activity (converted to mouse EGF, ng/ml) |
|---|---|
| A9/1515-4 | 43 |
| A9/1515-14 | 566 |
| A9/1515-17 | 208 |
| A9/1515-34 | 258 |
| A9/1515-63 | 94 |

REFERENCE EXAMPLE 5
Purification of BTC Produced by A9 Cells

Figure 5:
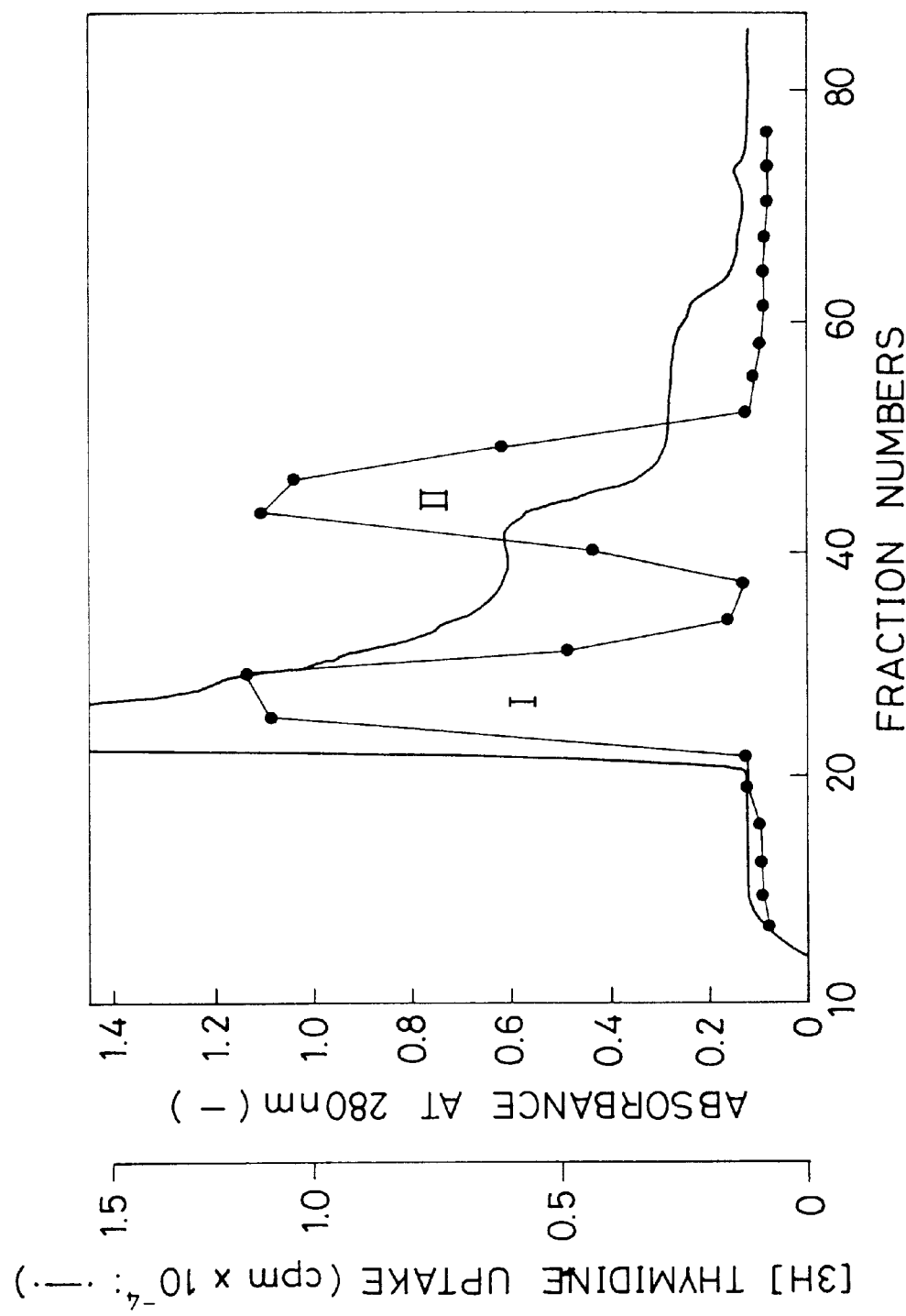
FIG. 5 is a graph showing results of S-Sepharose column chromatography and DNA synthesis induction activity obtained in Reference Example 5.

To 3.5 liters of a culture supernatant of the A9/1515-14 cells, 180 ml of 1 M potassium phosphate (pH 6.0), 7 ml of 0.5 M EDTA, 36 ml of 5% CHAPS and 7 ml of 0.25 M PMSF were added, and the resulting mixture was loaded on an S-Sepharose column (2.6 cm in diameter×40 cm, Pharmacia). After the column was washed with 300 ml of a buffer [0.1 M potassium phosphate (pH 6.0), 1 mM EDTA, 0.05% CHAPS and 0.5 mM PMSF], the above-mentioned buffer containing 0.7 M NaCl was allowed to flow through the column at a flow rate of 1 ml/minute to elute a protein. As to respective fractions collected for every 5 ml, the DNA synthesis induction activity (biological activity) of BALB/c3T3 cells was examined, and fraction Nos. 23–32 and 40–49 were pooled as BTC-I and BTC-II, respectively (FIG. 5).

Figure 6:
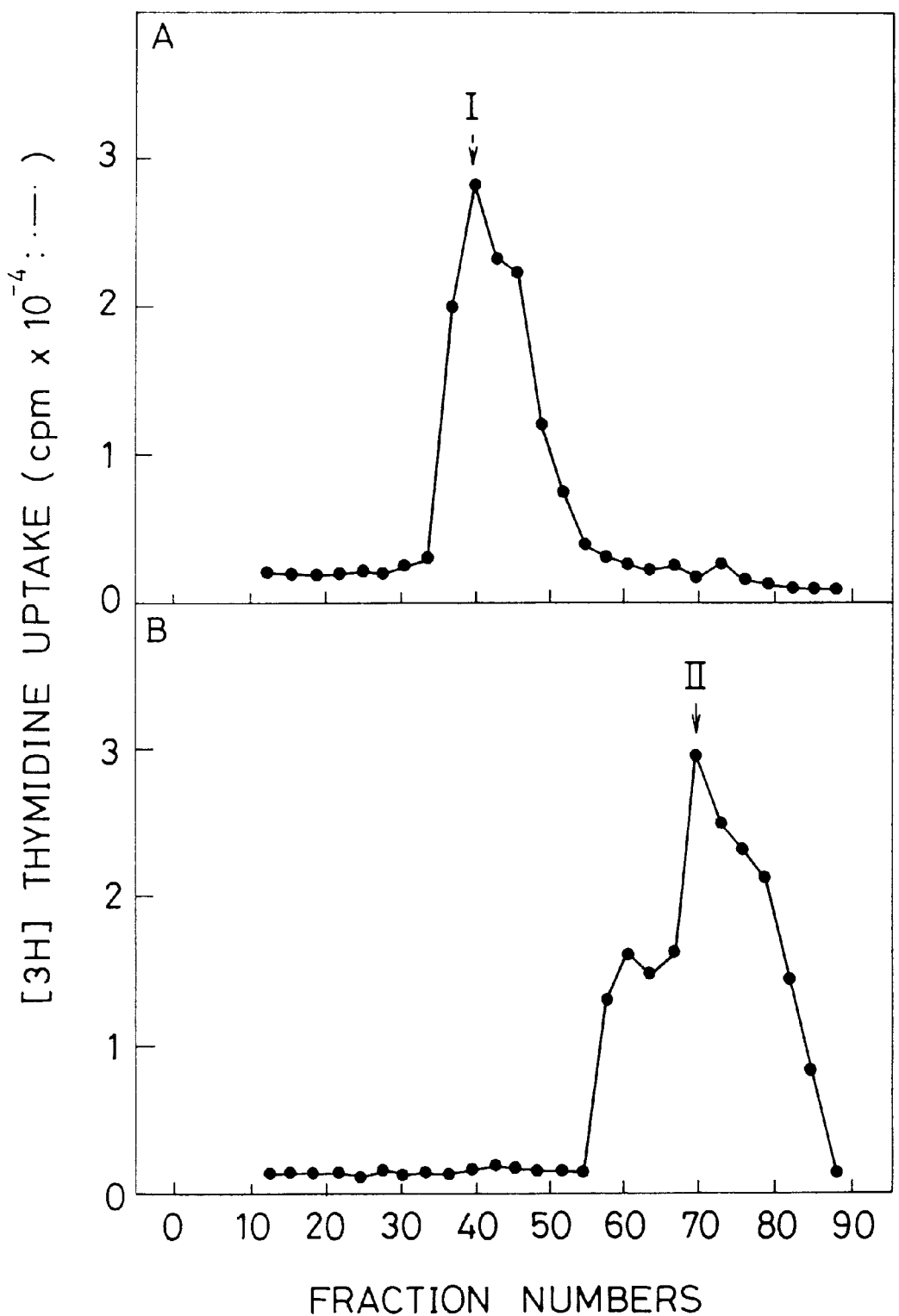
FIG. 6 is a graph showing results of gel filtration obtained in Reference Example 5.

The BTC-I pool fraction obtained from the S-Sepharose column was fractionated with 25% and 80% solutions of ammonium sulfate, followed by concentrating by ultrafiltration (Centriprep-10, Amicon). The concentrate was loaded at a flow rate of 1.2 ml/minute on a gel filtration column (1.6 cm in diameter×60 cm; Superdex 75 pg, Pharmacia) equilibrated with 20 mM Tris (pH 7.4), 1 mM EDTA and 0.05% CHAPS, and fractions were collected for every 1.2 ml from 15 minutes after the flowing initiation. A fraction which showed high biological activity (fraction No. 35–41) was pooled (FIG. 6A).

The BTC-II pool fraction obtained from the S-Sepharose column was concentrated by ultrafiltration (YM2, Amicon). The concentrate was loaded at a flow rate of 1.2 ml/minute on a gel filtration column (1.6 cm in diameter×60 cm; Superdex 75 pg, Pharmacia) equilibrated with 20 mM Tris (pH 7.4), 1 mM EDTA and 0.05% CHAPS, and fractions were collected from 15 minutes after initiation for every 1.2 ml. A fraction which showed high biological activity (fraction No. 66–74) was pooled (FIG. 6B).

Figure 7:
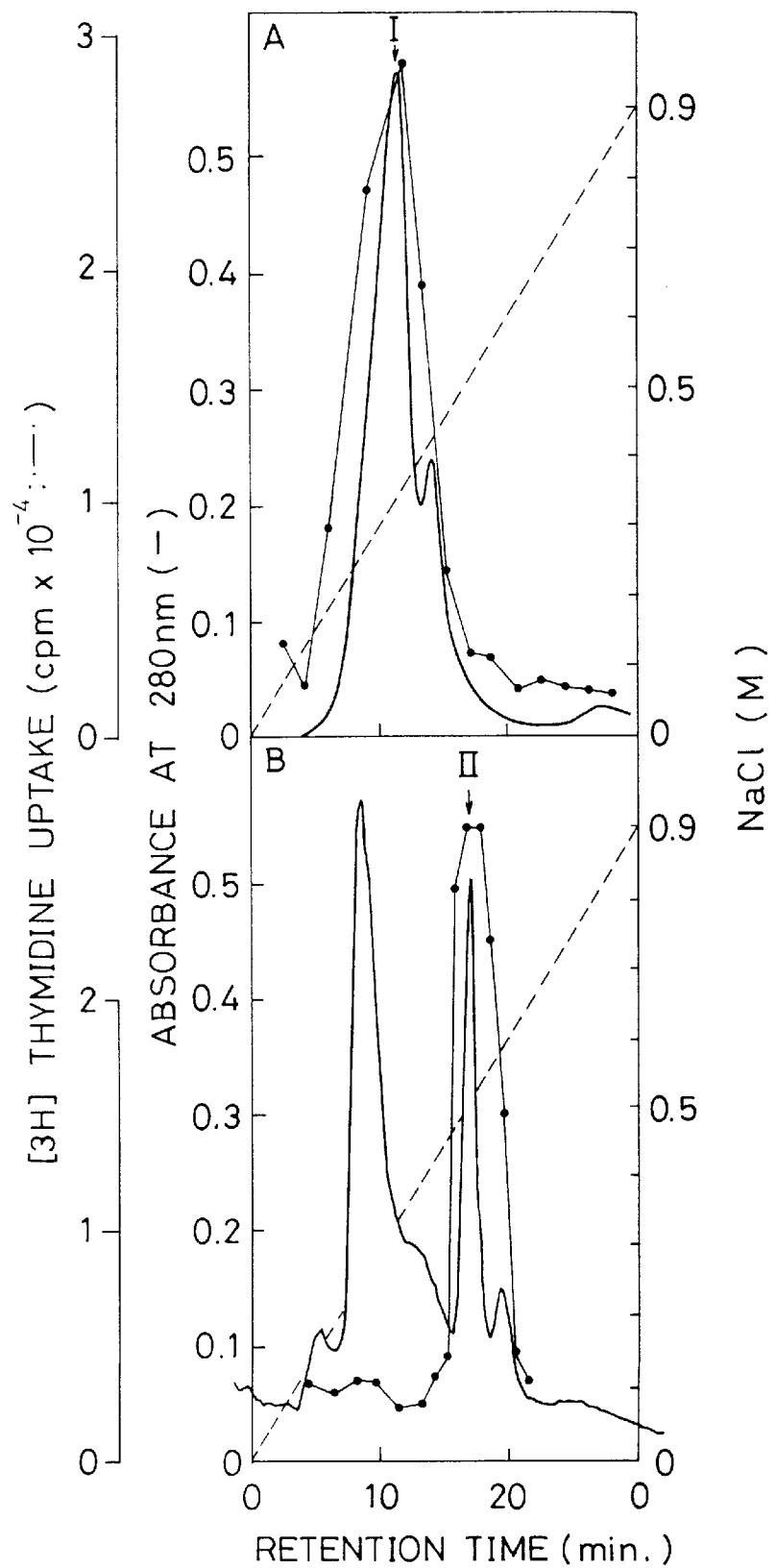
FIG. 7 is a graph showing results of heparin high performance liquid column chromatography obtained in Reference Example 5.

The BTC-I poli fraction collected from the gel filtration column was loaded on a heparin HPLC column (0.8 in diameter×5 cm; AFpak HR-894, Showa Denko K. K., Japan). The column was washed with 20 mM Tris-HCl (pH 7.4), 1 mM EDTA and 0.05% CHAPS, and then eluted with a linear gradient of 0–0.9 M NaCl at a flow rate of 1 ml/minute for 30 minutes to fractionate an eluate for every 1 ml. Fractions of fraction Nos. 9 to 13 in which biological activity was observed were pooled (FIG. 7A).

The BTC-II pool fraction collected from the gel filtration column was loaded on a heparin HPLC column (0.8 in diameter×5 cm; AFpak HR-894, Showa Denko K. K., Japan). The column was washed with 20 mM Tris-HCl (pH 7.4), 1 mM EDTA and 0.05% CHAPS, and thereafter eluted with a linear gradient of 0–0.9 M NaCl at a flow rate of 1 ml/minute for 30 minutes to fractionate an eluate for every 1 ml. Fractions of fraction Nos. 16 to 19 in which biological activity was observed were pooled (FIG. 7B).

Figure 8:
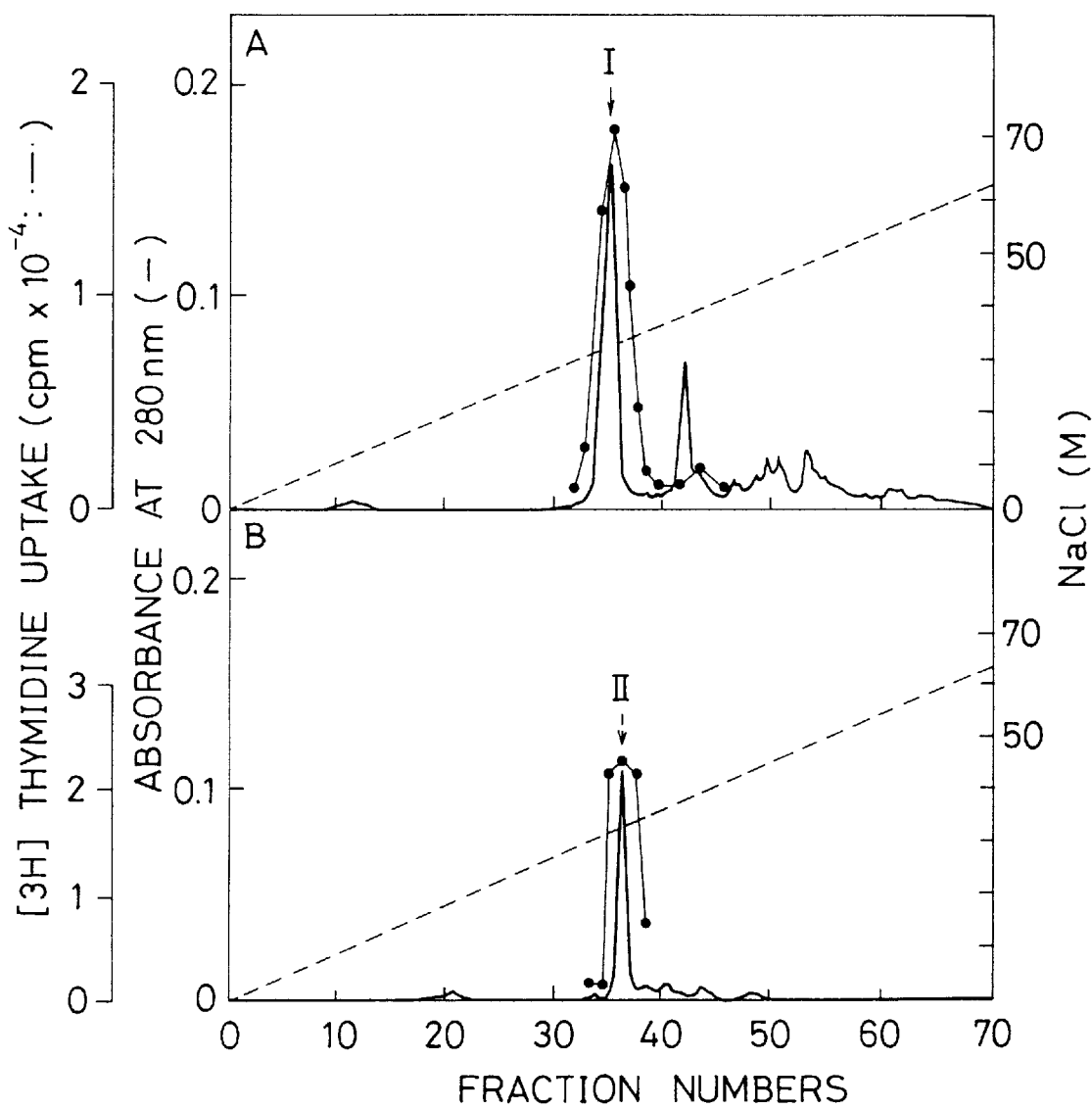
FIG. 8 is a graph showing results of reverse high performance liquid chromatography obtained in Reference Example 5.
Figure 9A:
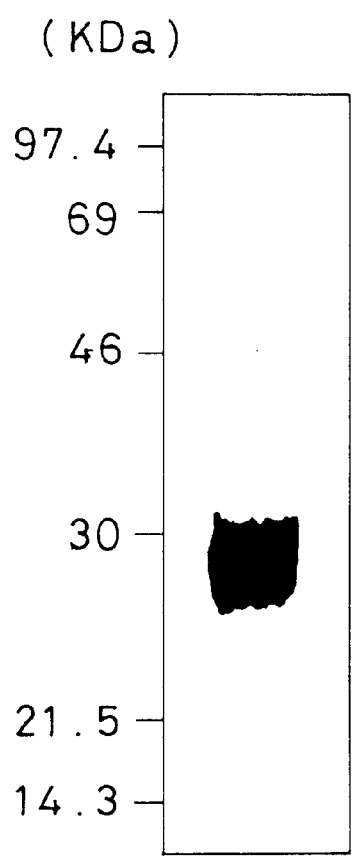
FIGS. 9A–9B shows results of SDS-PAGE silver staining obtained in Reference Example 5.

TFA was added to the BTC-I pool fraction collected from the heparin column to give a final concentration of 0.1%, and the TFA-containing fraction was loaded on a C18 reverse phase HPLC column (0.46 cm in diameter×15 cm; Asahipak ODP-50, Asahi Chemical, Japan). Elution was performed with a linear gradient of 0–63% acetonitrile in the presence of 0.1% TFA for 70 minutes, and an eluate was collected for every 0.5 ml (1 minute) (FIG. 8A). Biological activity was observed in agreement with elution peaks of the protein. The protein in this portion was examined by SDS-PAGE/silver staining. As a result, a band was detected only at the position corresponding to a molecular weight of 26 to 30 k (FIG. 9A).

By the above-mentioned operation, 150 μg of BTC-I was obtained.

Figure 9B:
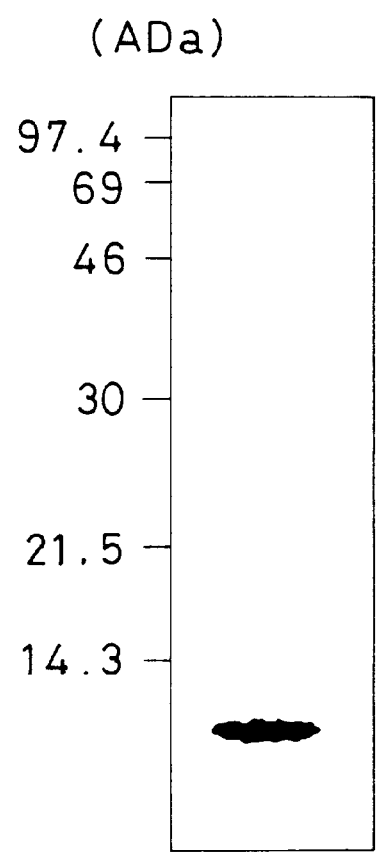

TFA was added to the BTC-II pool fraction collected from the heparin column to give a final concentration of 0.1%, and the TFA-containing fraction was loaded on a C18 reverse phase HPLC column (0.46 cm in diameter×15 cm; Asahipak ODP-50, Asahi Chemical, Japan). Elution was performed with a linear gradient of 0–63% acetonitrile in the presence of 0.1% TFA for 70 minutes, and an eluate was collected for every 0.5 ml (1 minute) (FIG. 8B). Biological activity was observed in agreement with elution peaks of the protein. The protein in this portion was examined by SDS-PAGE/silver staining. As a result, a band was detected only at the position corresponding to a molecular weight of 14 k (FIG. 9B).

By the above-mentioned operation, 75 μg of BTC-II was obtained.

REFERENCE EXAMPLE 6
Purification of BTC Produced from Recombinant *E. coli*

*E. coli* MM294(DE3)/plysS, pTB1516 was cultivated overnight, and thereafter, LB medium was inoculated with the culture cell solution in a 20-fold dilution. After cultivation at 37° C. for 2 hours, IPTG was added to give a final concentration of 0.1 mM, followed by further cultivation for 3 hours. Cells were collected by centrifugation, and stored at −20° C. until used.

Figure 10:
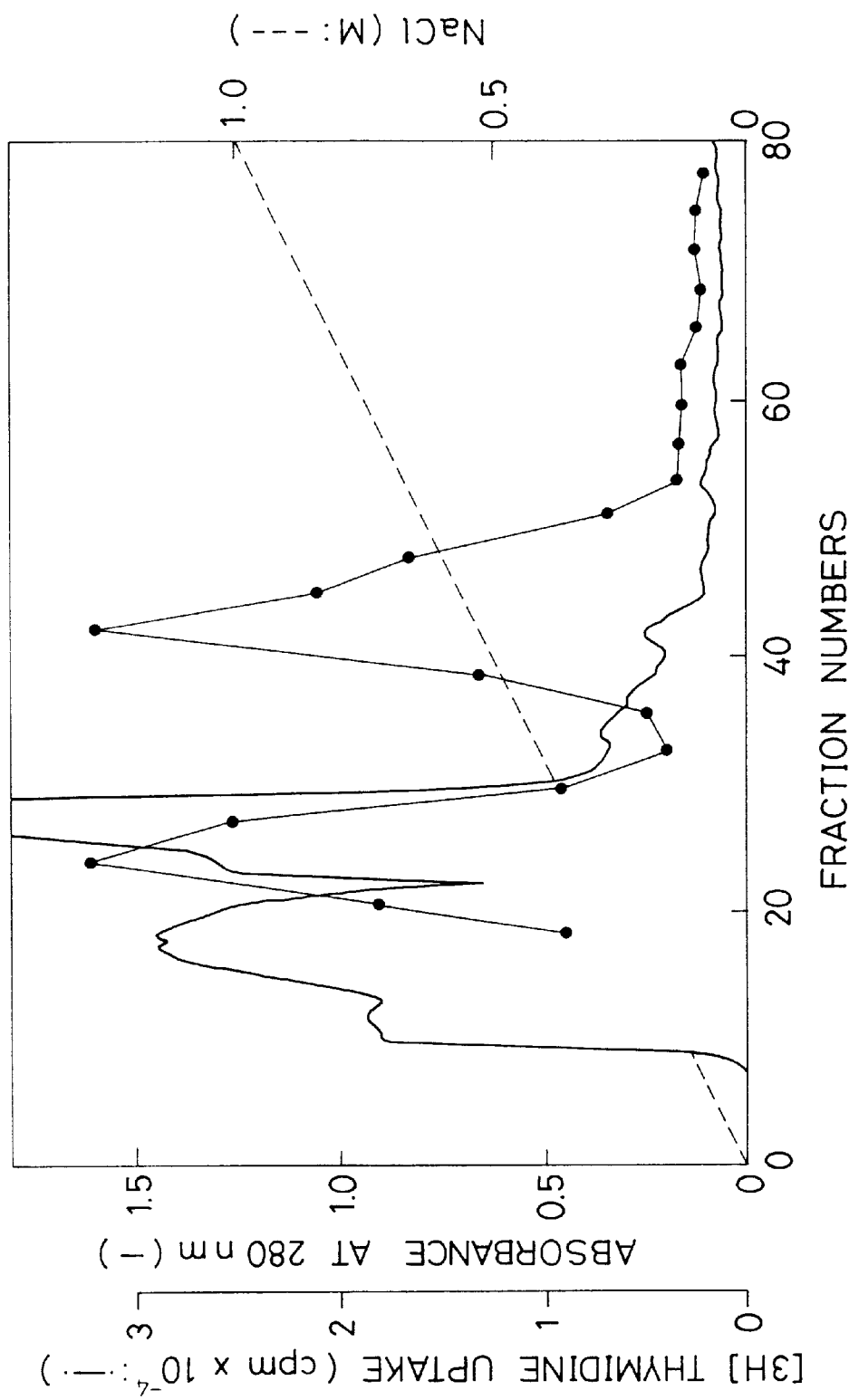
FIG. 10 is a graph showing results of S-Sepharose column chromatography obtained in Reference Example 6.

The cell stock corresponding to the 5-liter culture was defrosted, and suspended in 300 ml of an ice-cooled buffer containing 50 mM Tris-HCl (pH 7.4), 10 mM EDTA, 0.2 M NaCl, 10% sucrose and 1 mM APMSF. Then, 40 mg of egg white lysozyme was dissolved therein. After incubation at 4° C. for 2 hours, the suspension was subjected to ultrasonic treatment, and centrifuged at 20,000×g for 1 hour to obtain a supernatant. This supernatant was allowed to pass through a 200-ml Q-Sepharose bed, and then TCA was added thereto to give a final concentration of 4%, followed by standing at 40° C. for 10 minutes. A precipitate collected by centrifugation at 20,000×g for 20 minutes was suspended in 100 ml of a buffer containing 20 mM Tris (pH 7.4), 1 mM EDTA, 0.15 M NaCl and 1 mM APMSF, and 5 M NaOH was added to the resulting suspension while homogenizing it with a moter to adjust the pH to 6. This homogenate was centrifuged at 100,000×g for 1 hour to obtain a supernatant, which was loaded on an S-Sepharose column (1.6 cm in diameter× 10 cm, Pharmacia). The column was washed with a buffer containing 0.1 M potassium phosphate (pH 6.0), 1 mM EDTA and 0.5 mM PMSF, and thereafter eluted with 400 ml linear gradient of NaCl from 0 to 1 M for 200 minutes. An eluate was collected for every 5 ml. Fraction Nos. 20 to 27 and fraction Nos. 40 to 45 in which high biological activity was observed were pooled as $E.\ coli$ BTC-I and $E.\ coli$ BTC-II fractions, respectively (FIG. 10).

Figure 11:
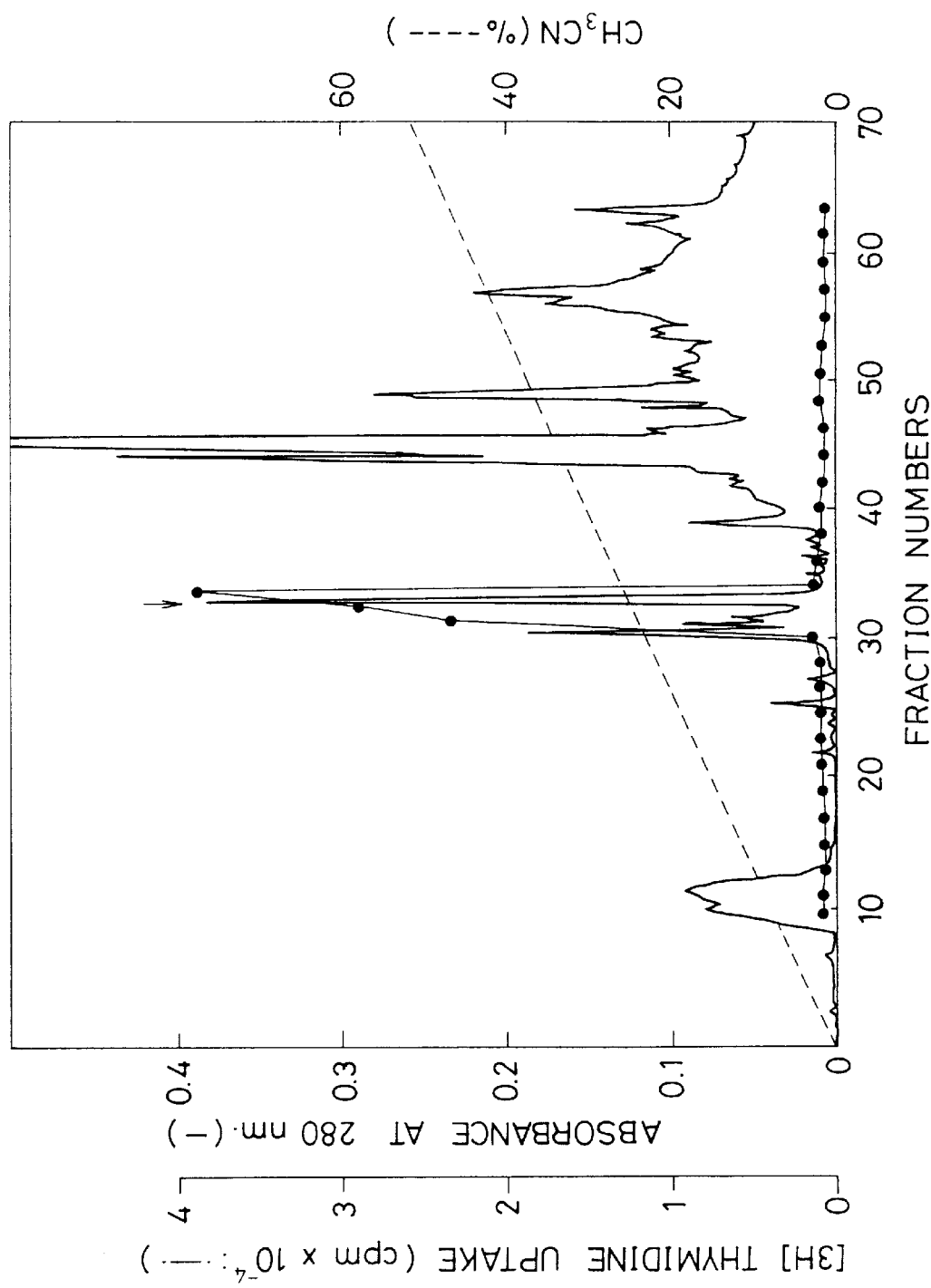
FIG. 11 is a graph showing results of reverse high performance liquid column chromatography obtained in Reference Example 6.
Figure 12:
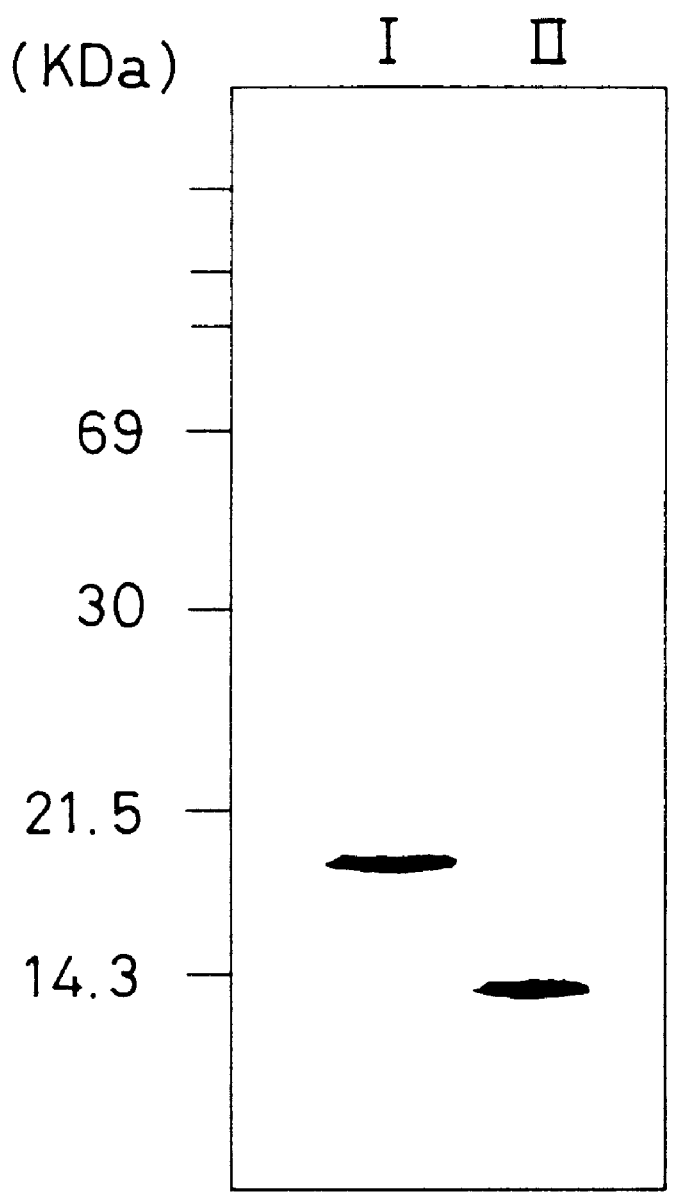
FIG. 12 shows results of SDS-PAGE silver staining obtained in Reference Example 6.

TFA was added to the BTC-I pool fraction to give a final concentration of 0.1%, and the TFA-containing fraction was loaded on a C18 reverse phase HPLC column (1.0 cm in diameter×25 cm; Asahipak ODP-50, Asahi Chemical, Japan). The column was washed with 0.1% TFA, and thereafter eluted with 340 ml linear gradient of acetonitrile from 0% to 63% for 170 minutes. Then, an eluate was collected for every 4 ml. Biological activity was observed in agreement with the peak indicated by the arrow (FIG. 11). This peak was examined by SDS-PAGE/silver staining. As a result, a band was observed at the position corresponding to a molecular weight of about 18 k (FIG. 12, lane I). BTC-I was purified. By this method, 630 μg of $E.\ coli$ BTC-I was obtained.

Figure 13:
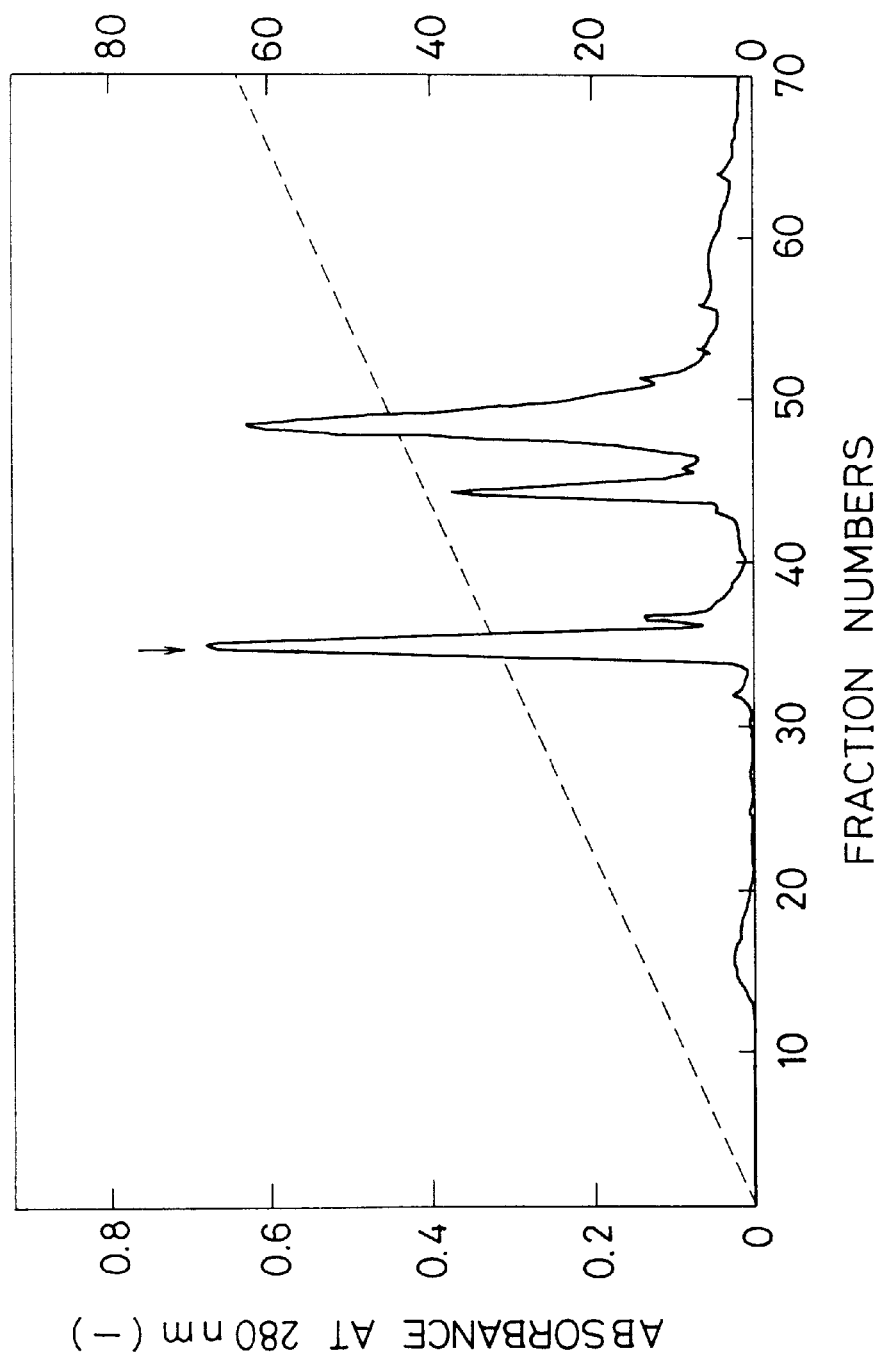
FIG. 13 is a graph showing results of reverse high performance liquid column chromatography obtained in Reference Example 6.

The BTC-I pool fraction was loaded on a C18 reverse phase HPLC column (4.6 cm in diameter×15 cm; Asahipak ODP-50, Asahi Chemical, Japan) in the presence of 0.1% TFA. After washing, the column was eluted with 35 ml linear gradient of acetonitrile from 0% to 63% for 70 minutes, and an eluate was collected for every 0.5 ml. Biological activity was observed in agreement with the peak indicated by the arrow (FIG. 13). This peak was examined by SDS-PAGE/silver staining. As a result, a band was observed at the position corresponding to a molecular weight of less than 14.3 k (lysozyme) (FIG. 12, lane II). BTC-II was purified. By this method, 990 μg of $E.\ coli$ BTC-II was obtained.

N-terminal amino acid sequences of $E.\ coli$ BTC-I SEQ ID NO:9 and $E.\ coli$ BTC-II SEQ ID NO:10 were determined up to 20 amino acid residues. The results showed that BTC-I had an N-terminal sequence starting from translation initiation methionine as expected, and that BTC-II had a molecule lacking 31 residues at the N-terminal side (FIG. 14).

EXAMPLE 1

Immunization

Human BTC-I obtained in Reference Example 6 described above was dissolved in physiological saline, and the resulting solution was thoroughly suspended in an equivalent volume of Freund's complete adjuvant to prepare a suspension. The suspension was given intracutaneously to BALB/c mice (female, 10 weeks old) in a dose of 50 μg of antigen human BTC-I per mouse to perform an initial immunization. After 3 weeks, a suspension of human BTC-I in Freund's incomplete adjuvant was prepared and given to the mice in a manner similar to that of the initial immunization, thereby performing additional immunization. The booster was further conducted twice for every 2 weeks, and after 3 weeks, 50 μg of human BTC-I dissolved in physiological saline was given intraperitoneally to the mice to perform a final immunization.

EXAMPLE 2

(1) Cell Fusion

Three days after the final immunization, the spleens were removed from the mice immunized in Example 1 to obtain spleen cells to be used for cell fusion. These cells were suspended in RPMI 1640 medium (Nippon Seiyaku, Japan).

Mouse myeloma cells P3X63Ag 8UI (P3U1) were subcultured in RPMI 1640 medium supplemented with 10% fetal calf serum (FBS, Hyclon Laboratories). Cell fusion was carried out according to the method established by Köhler and Milstein [G. Köhler and C. Milstein, *Nature*, 256, 495 (1975)]. The resulting spleen cells and the mouse myeloma cells were mixed in a ratio of 5:1. After sufficient removal of the medium, the mixture was incubated at 37° C. for 2 minutes in 50% polyethylene glycol 4000 (Sigma) dissolved in 1 ml of PRMI 1640 medium. The resulting cells were washed with serum-free RPMI 1640 medium, and then suspended in RPMI-1640 medium (containing 10% FBS) supplemented with HAT ($1\times10^{-4}$ M hypoxanthine, $4\times10^{-7}$ M aminopterin and $1.6\times10^{-5}$ M thymidine) (hereinafter referred to as HAT medium). The suspension was dispensed into each well of a 96-well culture plate by each $3\times10^5$ cells/0.1 ml. After cultivation at 37° C. in 7% $CO_2$ for 3 days, 0.1 ml of HAT medium was further added to each well. The cells which grew under these conditions were hybridomas.

(2) Screening for Antibody-Producing Cells

Physiological saline containing 10 μg/ml of BTC-I obtained in Reference Example 5 was added in an amount of 0.1 ml to each well of a 96-well flat-bottomed ELISA plate (Falcon 3912), followed by standing at 4° C. overnight. After washing three times with 0.05% Tween 20-PBS, 0.2 ml of 5 mg/ml BSA-0.05% Tween 20-PBS was added to each well, followed by standing at 37° C. for 1 hour. A culture supernatant which was subjected to a serial 2-fold stepwise dilution with 0.05% Tween 20-PBS was added in an amount of 0.1 ml/well, and the plate was allowed to stand at room temperature for 2 hours. After washing three times with 0.05% Tween 20-PBS, 0.1 ml of an HRP-labeled anti-mouse IgG rabbit antibody solution (1 μg/ml) was added to each well as a secondary antibody, followed by standing at room temperature for 1 hour. After washing was repeated 5 times, 0.1 ml of a color-developing solution (prepared by mixing 10 ml of o-phenylenediamine, 10 ml of 50 mM disodium phosphate-24 mM citrate buffer and 120 μl of a 1.7% hydrogen peroxide solution at the time of use) was added to each well to conduct HRP enzyme reaction. The enzyme reaction was terminated by addition of 0.05 ml of 6 N sulfuric acid, and the absorbance at a wavelength of 492 nm was measured (ELISA).

By this assay, primary screening was performed for culture supernatants of wells in which the hybrid cells grew, and cells in wells which exhibited high absorbance were cloned by the limiting dilution analysis. In cloning, the cells were preliminarily cultivated at 37° C. in 7% $CO_2$ overnight. Mouse peritoneal exudate cells ($10^4$ cells/well) were used as a feeder. Screening and cloning were further repeated to obtain anti-human BTC antibody-producing hybridomas 1A1, 2B2 and 5E5. When the antibody titer was assayed for hybridoma culture supernatants by the above-mentioned ELISA, the absorbance at a wavelength of 492 nm was 1 or more even when 128-fold dilutions were made. The cloned hybridoma cells were suspended in RPMI-1640 medium supplemented with 20% fetal calf serum and 10% dimethyl sulfoxide (DMSO) and stored in liquid nitrogen.

EXAMPLE 3
Immunoglobulin Class of Monoclonal Antibodies

Culture supernatants of the hybridoma cells obtained in Example 2-(2) were tested by a mouse antibody subclass detecting kit (Bio RAD) to determine immunoglobulin subclass. Results are shown in Table 3.

TABLE 3

| Immunoglobulin | Hybridoma culture supernatant | | |
|---|---|---|---|
| subclass | 1A1 | 2B2 | 5E5 |
| IgG1 | + | + | + |
| IgG2a | – | – | – |
| IgG2b | – | – | – |
| IgG3 | – | – | – |
| IgM | – | – | – |
| IgA | – | – | – |

In Table 3, "+" indicates the positive reaction, and "–" indicates the negative reaction.

The results shown in Table 3 reveal that three kinds of antibodies in the hybridoma culture supernatants belong to IgG1.

EXAMPLE 4
Recognition Site of Monoclonal Antibody

To each well of a 96-well flat-bottomed ELISA plate (Falcon 3912), 0.1 ml of physiological saline containing 1 μg/ml of BTC-I or BTC-II obtained in Reference Example 5 was added, followed by standing at 4° C. overnight. After three time washings with 0.05% Tween 20-PBS, 0.2 ml of 5 mg/ml BSA-0.05% Tween 20-PBS was added to each well, followed by standing at 37° C. for 1 hour. After three time washings with 0.05% Tween 20-PBS again, a culture supernatant which was subjected to a serial 2-fold stepwise dilution with 0.05% Tween 20-PBS was added in an amount of 0.1 ml/well, and the plate was allowed to stand at room temperature for 2 hours. After three time washings with 0.05% Tween 20-PBS, 0.1 ml of an HRP-labeled anti-mouse IgG rabbit antibody solution (1 μ/ml) was added to each well as a secondary antibody, followed by standing at room temperature for 1 hour. After washing was repeated 5 times, 0.1 ml of a color-developing solution (prepared by mixing 10 ml of o-phenylenediamine, 10 ml of 50 mM disodium phosphate-24 mM citrate buffer and 120 μl of a 1.7% hydrogen peroxide solution at the time of use) was added to each well to conduct HRP enzyme reaction. The enzyme reaction was terminated by addition of 0.05 ml of 6 N sulfuric acid, and the absorbance at a wavelength of 492 nm was measured (ELISA). Results are shown in Table 4.

TABLE 4

| | Hybridoma culture supernatant | | |
|---|---|---|---|
| | 1A1 | 2B2 | 5E5 |
| Human BTC-I | + | + | + |
| Human BTC-II | + | + | + |

In Table 4, "+" indicates the positive reaction, and "–" indicates the negative reaction.

The results shown in Table 4 reveal that three kinds of antibodies in the hybridoma culture supernatants recognize the C-terminal side from $Arg^{62}$ of human BTC (+31 in FIG. 3).

EXAMPLE 5
Reaction Specificity of Monoclonal Antibody

To each well of a 96-well flat-bottomed ELISA plate (Falcon 3912), 0.1 ml of physiological saline containing 1 μg/ml of BTC-I obtained in Reference Example 5, Human TGF-α (Gibco-BRL), human EGF (Boehringer Mannheim) or mouse EGF (Takara Shuzo, Japan) was added, followed by standing at 4° C. overnight. After three time washings with 0.05% Tween 20-PBS, 0.2 ml of 5 mg/ml BSA-0.05% Tween 20-PBS was added to each well, followed by standing at 37° C. for 1 hour. After three time washings with 0.05% Tween 20-PBS again, a culture supernatant which was subjected to a serial 2-fold stepwise dilution with 0.05% Tween 20-PBS was added in an amount of 0.1 ml/well, and the plate was allowed to stand at room temperature for 2 hours. After three time washings with 0.05% Tween 20-PBS, 0.1 ml of an HRP-labeled anti-mouse IgG rabbit antibody solution (1 μg/ml) was added to each well as a secondary antibody, followed by standing at room temperature for 1 hour. After five time washings were repeated, 0.1 ml of a color-developing solution (prepared by mixing 10 ml of o-phenylenediamine, 10 ml of 50 mM disodium phosphate-24 mM citrate buffer and 120 μl of a 1.7% hydrogen peroxide solution at the time of use) was added to each well to conduct HRP enzyme reaction. The enzyme reaction was terminated by addition of 0.05 ml of 6 N sulfuric acid, and the absorbance at a wavelength of 492 nm was measured (ELISA). Results are shown in Table 5.

TABLE 5

| | Hybridoma culture supernatant | | |
|---|---|---|---|
| | 1A1 | 2B2 | 5E5 |
| BTC-I | + | + | + |
| Human TGF-α | – | – | – |
| Human EGF | – | – | – |
| Mouse EGF | – | – | – |

In Table 5, "+" indicates the positive reaction, and "–" indicates the negative reaction.

The results shown in Table 5 reveal that three kinds of antibodies in the hybridoma culture supernatants specifically recognize BTC.

EXAMPLE 6
Purification of Monoclonal Antibody from Culture Supernatant

A 1:1 mixture of the culture supernatant of mouse hybridoma 1A1, 2B2 or 5E5 obtained in Example 2 and a binding buffer [3 M sodium chloride and 1.5 H glycine (pH 8.7)] was loaded onto a protein A column equilibrated with the binding buffer to allow an antibody to be adsorbed thereby. After washing with the binding buffer, the antibody was eluted with an eluting buffer [0.1 M citric acid (pH 5)]. 1 M Tris (pH 8.0) was added to the eluate to neutralize it, followed by dialysis with phosphate buffered saline. Thus, purified monoclonal antibody 1A1, 2B2 or 5E5 was obtained.

EXAMPLE 7
Assay of Human BTC-Neutralizing Activity

For antibodies 1A1, 2B2 and 5E5 purified in Example 6, neutralizing activity on human BTC was assayed. Mouse Balb/c 3T3 clone A31-714-4 cells were seeded on a 96-well plate at 2×10³ cells per well, and cultivated in 100 μl of DMEM supplemented with 5% fetal calf serum. The next day, the medium was changed by DMEM supplemented with 1% FCS, and cultivation was further continued for 3 days. Then, 1 ng/ml of purified human BTC-I, as well as 0.1, 1 and 10 μg/ml of the above-mentioned three kinds of monoclonal antibodies to human BTC, was added thereto. After cultivation for 18 hours, 0.5 μCi/well of ³H thymidine (5 Ci/mmol) was added, followed by cultivation for 6 hours. The culture solution was removed, and the cells were washed 3 times with PBS. Then, 100 μl of 5% SDS was added to dissolve the cells. The radioactivity taken into cell DNAs was measured by use of a liquid scintillation counter to assay the neutralizing activity of the respective monoclonal antibodies on the DNA synthesis induction ability due to human BTC. Results are shown in FIG. 15.

Figure 15:
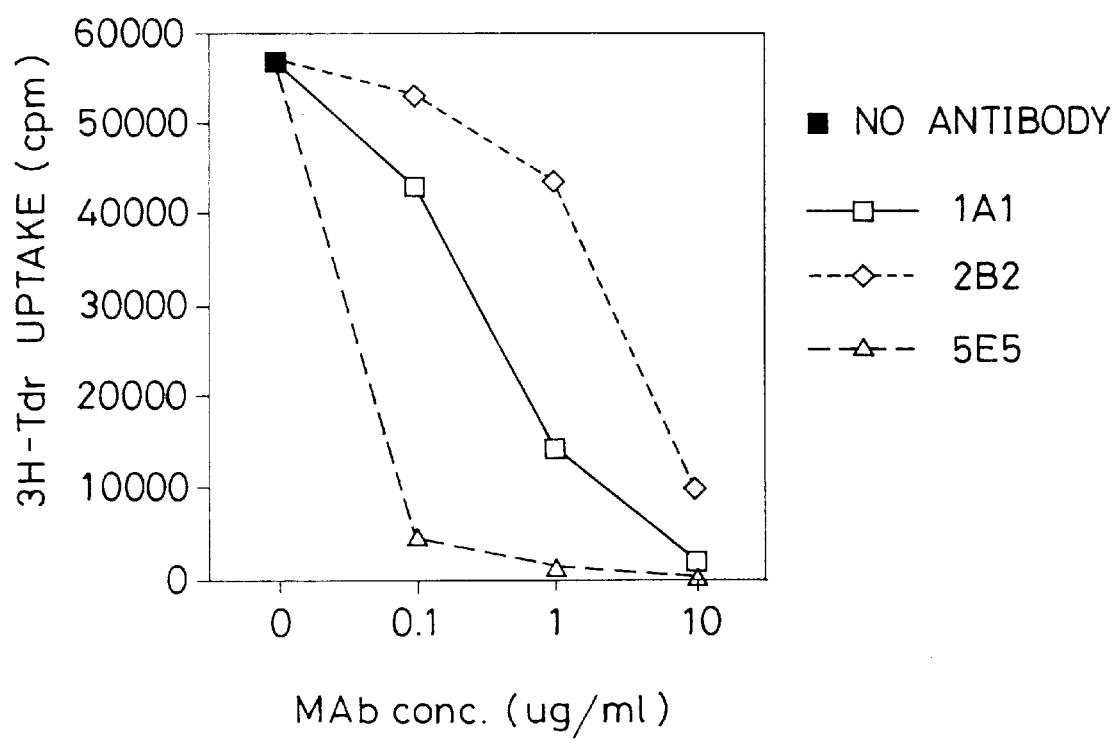
FIG. 15 is a graph showing the neutralizing activity of a monoclonal antibody of the invention on human BTC in Example 7.

Referring to FIG. 15, ■, □, ◇ and △ indicate the uptake values of ³H-thymidine when no antibody, antibody 1A1, antibody 2B2 and antibody 5E5 were added, respectively. All the monoclonal antibodies inhibited DNA synthesis of the cells when human BTC was added, depending on the concentration. In particular, antibody 5E5 exhibited high neutralizing activity.

On the other hand, similar experiments were conducted for human EGF, human TGF-α, human HB-EGF and mouse BTC belonging to the same EGF family. The DNA synthesis of A31 cells induced by addition of 1 ng/ml of each growth factor was not inhibited at all even when 10 μ/ml of antibody 1A1, 2B2 or 5E5.

The results described above proved that all of monoclonal antibodies 1A1, 2B2 and 5E5 specifically neutralized the biological activity of human BTC protein.

EXAMPLE 8

(1) One milligram of monoclonal antibody 5E5 obtained in Example 6 was dialyzed against 0.1 M NaHCO₃ (pH 8.0). Then, 120 μg of NHS-biotin (Vector, U.S.A.) dissolved in DMSO was added to the dialyzed antibody, followed by reaction at room temperature for 2 hours with stirring. After reaction, the reaction product was dialyzed against PBS(-) to remove unreacted NHS-biotin.

(2) Monoclonal antibody 1A1 obtained in Example 6 was diluted with 0.01 M Na₂HPO₄ (pH 8.0) supplemented with 0.01 M NaCl to a concentration of 10 μg/ml. The resulting solution was poured in an amount of 50 μl/well into an immunoplate (Nunc, Denmark), followed by standing overnight at 4° C. to allow it to be adsorbed by the plate. Antibodies not adsorbed were removed, followed by three time washings with PBS(-). A blocking solution [a solution prepared by diluting Block Ace (Dainippon Seiyaku, Japan) four times with PBS(-) and containing 0.01% Mlthiolate (trade mark)] in an amount of 100 μl/well. After standing at 4° C. overnight, the blocking solution was removed, followed by five time washings with PBS(-). Then, human BTC protein diluted with a diluent [a solution prepared by adding 0.2% Tween 20 to PBS(-)] was added in an amount of 50 μl/well, followed by reaction at 37° C. for 2 hours. After removal of unreacted BTC, the resulting product was washed 6 times with a washing solution [a solution prepared by adding 0.05% Tween 20 to PBS(μ)]. Further, biotinated monoclonal antibody 5E5 prepared in the above (1) was diluted 1:2000 with the diluent, and the diluted product was added in an amount of 50 μl/well, followed by reaction at 37° C. for 2 hours. After removal of an antibody-containing solution, the resulting product was washed 6 times with the washing solution, and avidin D-binding horseradish peroxidase (Vector, U.S.A.) diluted 1:1000 with the diluent was added in an amount of 50 μl/well, followed by reaction at room temperature for 30 minutes. After removal of the reaction solution, the resulting product was washed 8 times with the washing solution, and 50 μl/well of peroxidase substrate (Wako, Japan) was added to develop color. Thereafter, 50 μl/well of 2 N sulfuric acid was added to terminate reaction. After termination of the reaction, the calorimetric assay was performed.

Figure 16:
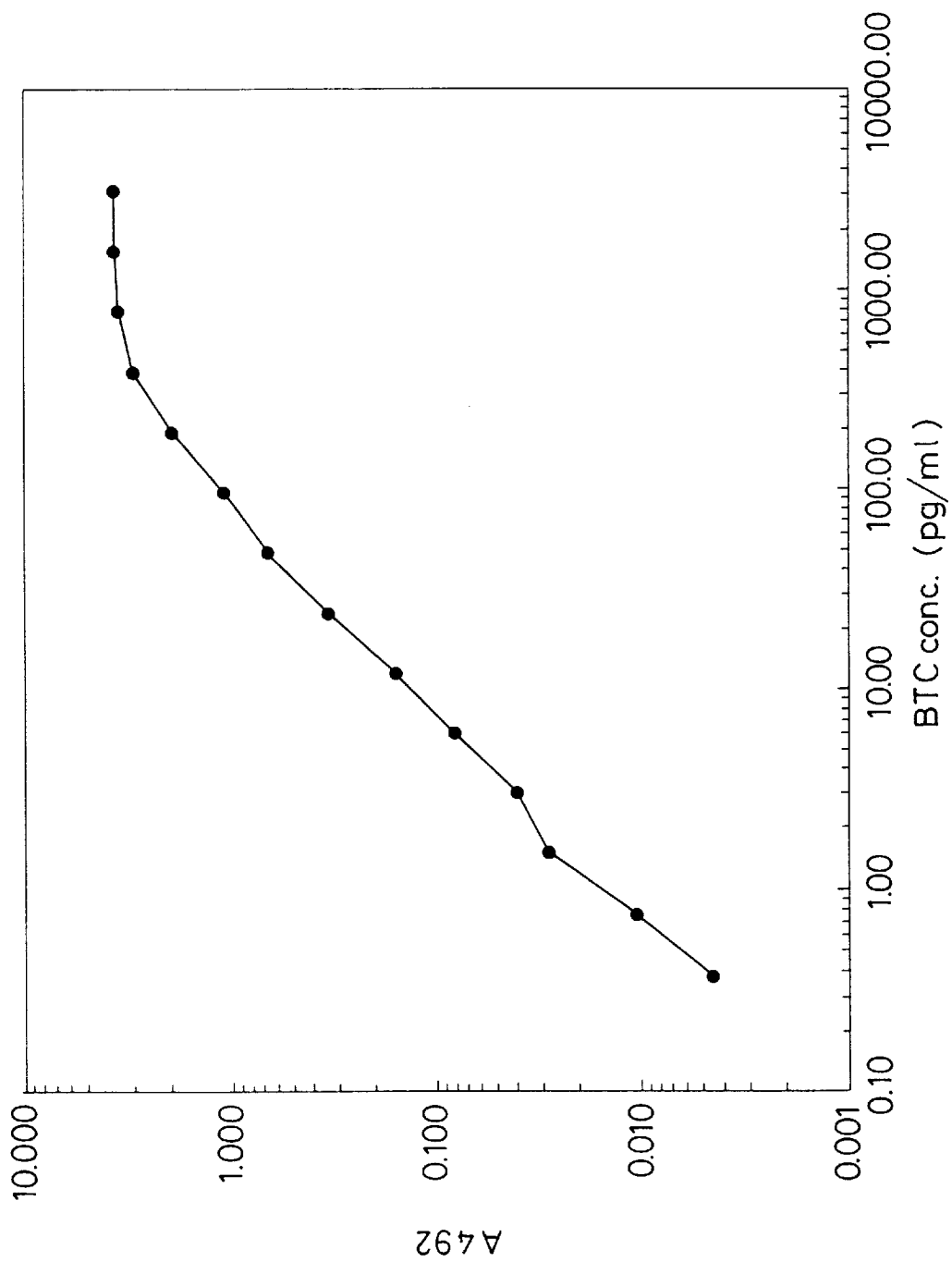
FIG. 16 is a graph showing a detection curve of human BTC.

FIG. 16 shows a detection curve of human BTC protein. The numbers on the abscissa indicate the concentration of human BTC protein added, and the numbers on the ordinate indicate the absorbance (at A492 nm) measured. The absorbance when BTC protein was not added was 0.06 to 0.07. When the concentration of human BTC showing an at least twice absorbance that was regarded as significant, the above-mentioned assay system was able to detect and determine human BTC having a concentration of 10 to 200 pg/ml.

In this assay system, human EGF, mouse EGF, human TGF-α, human HB-EGF and mouse BTC only showed background levels of absorbances, as shown in Table 6, which proved that this assay system was specific for human BTC protein.

TABLE 6

| Specimen | Concentration (ng/ml) | Absorbance ($A_{192}$) |
| --- | --- | --- |
| — | 0 | 0.062 |
| Human EGF | 1000 | 0.069 |
| Mouse EGF | 1000 | 0.064 |
| Human TGF-α | 1000 | 0.077 |
| Human HB-EGF | 1000 | 0.066 |
| Mouse BTC | 300 | 0.069 |
| Human BTC-I | 100 | 4.063 |
| Human BTC-I | 0.1 | 0.889 |

EXAMPLE 9
Purification of Human BTC Using Antibody Column

Twenty milligrams of monoclonal antibody 5E5 obtained in Example 6 was allowed to bind to 10 g of a wet gel of Formyl-Cellulofine (Seikagaku Corporation, Japan), and loaded onto an econo column to prepare an affinity column.

On the other hand, plasmid pTB1685 (a derivative of plasmid pTB1507 described in Reference Example 1; a plasmid in which the MULV-LTR region was changed to the human EF-1 promoter (*Nuclei Acids Res.*, 18, 5322), and the human BTC cDNA region was changed to the cDNA region coding for BTC-I having the amino acid sequence represented by SEQ ID NO: 1, using plasmid pTB1516 described in Reference Example 2 as a material) was introduced into hamster CHO DHFR⁻ cells, and human BTC high producing cell CHO 1685-39 was obtained from the cell lines converted to DHFR⁺. After the CHO 1685-39 cells were cultivated to a confluent in DMEM supplemented with 5% fetal calf serum and 35 μg/ml proline, the medium was changed by ASF medium (Ajinomoto, Japan), and the cells were further cultivated for 3 days, followed by recovery of a culture supernatant. Five liters of the culture supernatant was concentrated about 4-fold on an Amicon concentrator under ice cooling, and then the resulting concentrate was allowed to flow through the above-mentioned affinity column at a flow rate of 20 ml/hour to allow BTC to be adsorbed thereby. After adsorption, the column was washed with Dulbecco's phosphate buffer (PBS(-)) until the absorbance at 280 nm reached 0.05 or less. Then, the column was washed with 0.01 M phosphate buffer (pH 6.5) containing 0.5 M NaCl at the same flow rate. Further, the column was eluted with 0.05

M glycine-HCl (pH 2.3) containing 0.15 M NaCl at the same flow rate. The eluted fractions were neutralized with 1 M Tris-HCl (pH 8.0), and dialyzed against PBS(−).

The resulting fractions were subjected to 15% acrylamide electrophoresis [Laemmli, Nature, 277, 680 (1970)]. The Coomassie Blue staining method was employed for staining.

Figure 17:
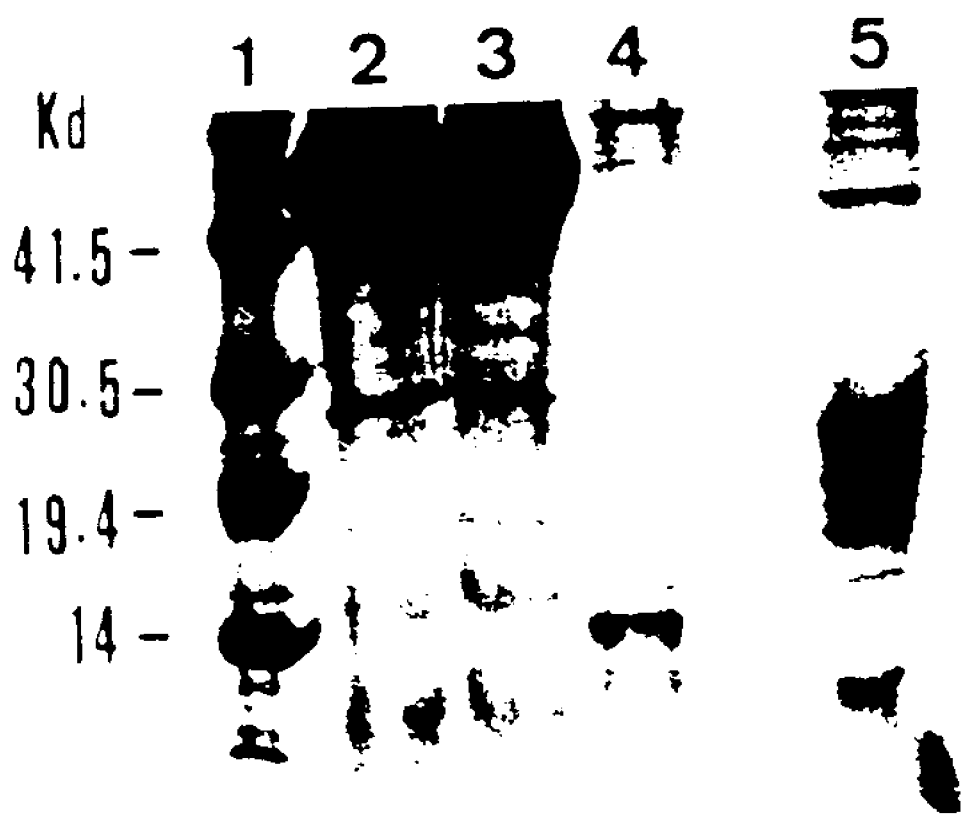
FIG. 17 shows results of Coomassie Blue staining obtained in Example 9.

FIG. 17 shows results for (1) a molecular weight marker, (2) the culture supernatant, (3) a fraction not adsorbed to the column, (4) a fraction eluted at a high salt-concentration (0.5 M NaCl) and (5) a fraction eluted with an eluting buffer.

Figure 18:
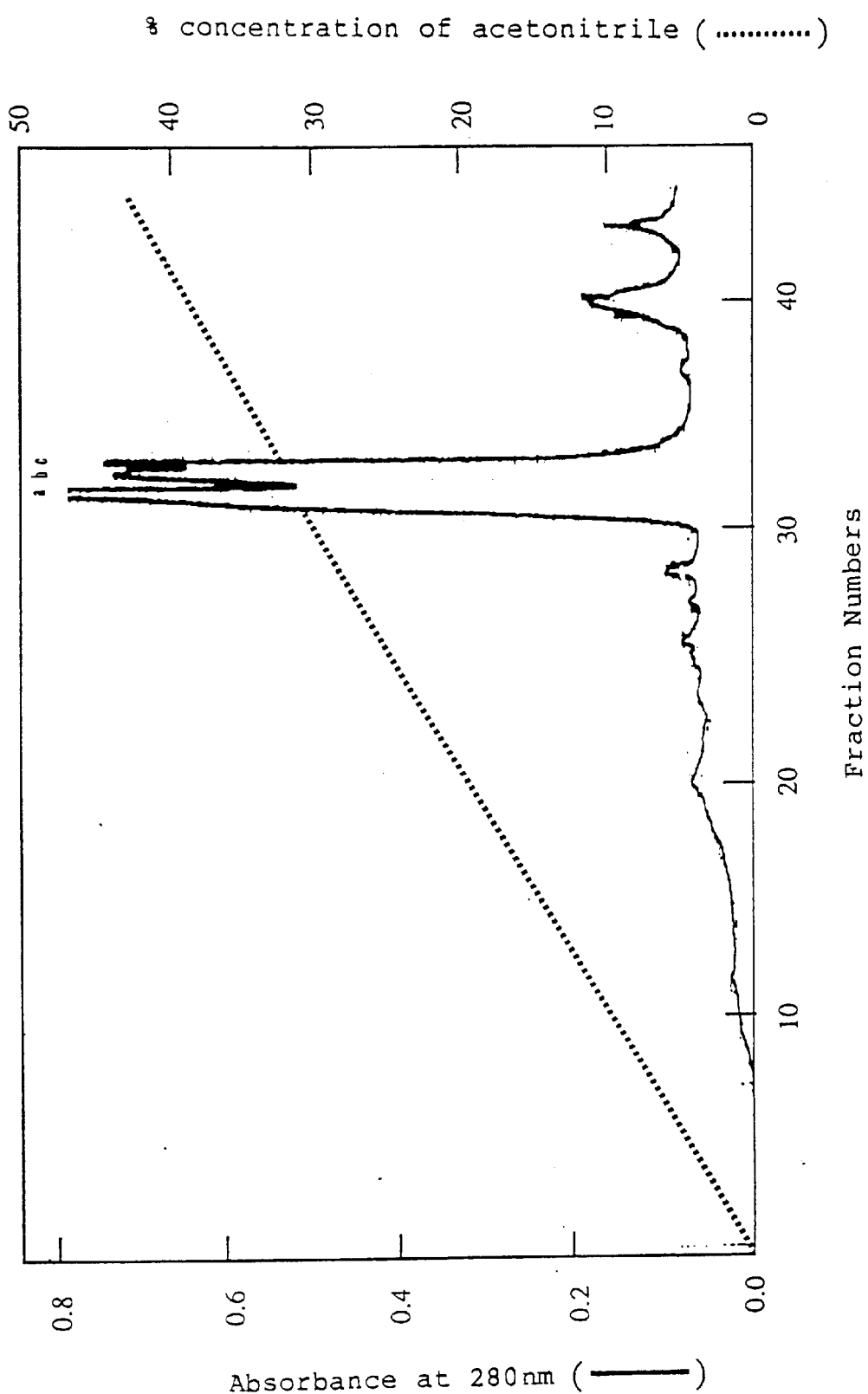
FIG. 18 is a graph showing results of reverse high performance liquid column chromatography obtained in Example 9.
Figure 19:
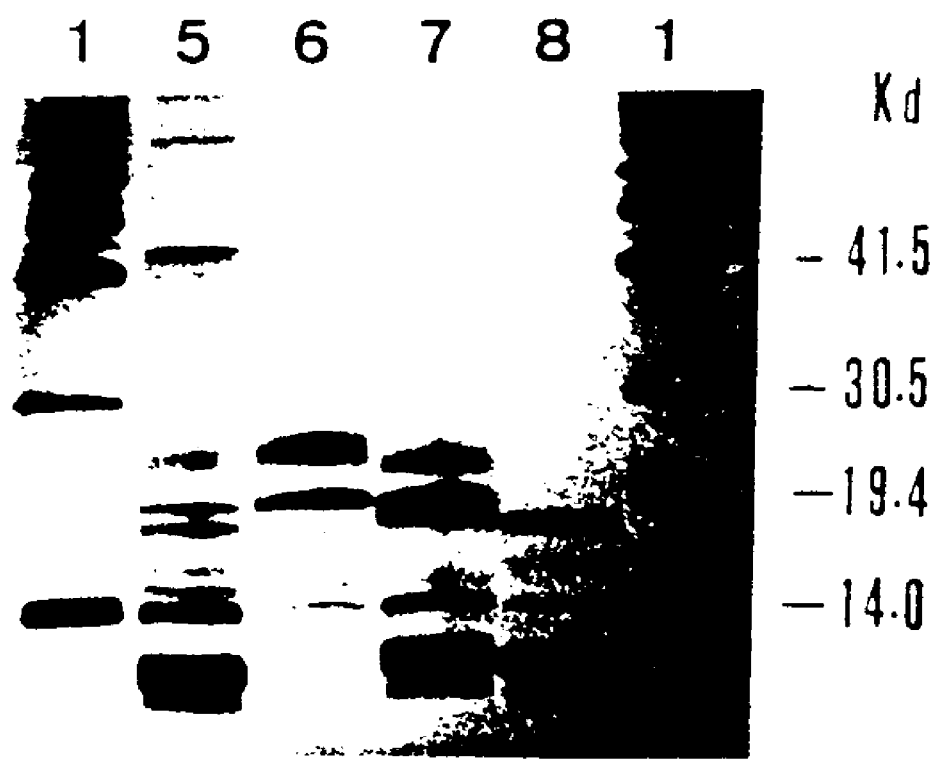
FIG. 19 shows results of silver staining obtained in Example 9.

Further, trifluoroacetic acid (TFA) was added to the eluted fraction (5) to give a final concentration of 0.05%, and the TFA-containing fraction was loaded on a TSK gel-ODS column (Tosoh, Japan). Elution was performed with a linear gradient of 0–60% acetonitrile in the presence of 0.05% TFA for 60 minutes, and an eluate was collected at 1 ml/minute (FIG. 18). Elution peaks a, b and c of the protein were subjected to 15% acrylamide electrophoresis, and stained by the silver staining method (FIG. 19). Numerals (1), (5), (6), (7) and (8) indicate the molecular weight marker, the fraction eluted from the affinity column, elution peak a, elution peak b and elution peak c, respectively.

For each fraction obtained in the above-mentioned purifying course, the amount of huma BTC protein was assayed by the method described in Example 8. Results are shown in Table 7.

TABLE 7

| Eluted fractions | Total amount of protein (A) (µg) | Amount of BTC (B) (µg) | (B)/(A) |
|---|---|---|---|
| Culture supernatant | 5360000 | 637.0 | 0.00012 |
| Concentrated culture supernatant (2) | 1582600 | 563.2 | 0.00036 |
| Fraction not adsorbed by affinity column (3) | 1267400 | 25.9 | 0.00002 |
| Fraction eluted with phosphate buffer (pH 6.5) + 0.5 M NaCl (4) | 336 | 1.9 | 0.00565 |
| Fraction eluted with 0.01 M glycine-HCl (pH 2.3) + 0.5 M NaCl (5) | 750 | 371.9 | 0.50 |
| Reverse phase HPLC | | | |
| Peak a (6) | 88 | 66.9 | 0.76 |
| Peak b (7) | 158 | 131.4 | 0.83 |
| Peak c (8) | 124 | 130.5 | 1.05 |

The biological activity of the above-mentioned eluted fractions was assayed by the uptake experiment of $^3$H-thymidine using the mouse Balb/c 3T3 cells described in Example 7. As a result, all the fractions showed DNA synthesis stimulating activity corresponding to the amount of human BTC protein.

The above results revealed that the use of the antibody columns using the antibody of the present invention allowed efficient purification of human BTC protein.

EXAMPLE 10

Preparation of Anti-Peptide Antibody (polyclonal antibody)

A polypeptide having the amino acid sequence from the 66th to the 80th of the amino acid sequence represented by SEQ ID NO: 1 was chemically synthesized to use it as an antigen.

(1) The above-mentioned peptide (5 mg) and hemocyanin (10 mg) were dissolved in 4 ml of 0.2 M phosphate buffer (pH 7.3), and 400 µl of 2.5% glutaraldehyde cooled in ice water was added thereto drop by drop with stirring. After stirring for 3 hours under ice cooling, the solution was dialyzed against distilled water to obtain a conjugate of the peptide and hemocyanin.

(2) Bovine serum albumin (BSA) (132 mg) was dissolved in 3 ml of 0.1 M phosphate buffer (pH 7.5) to obtain solution A. On the other hand, 11.2 mg of N-(γ-maleimidobutyloxy) succinimide (GMBS) was dissolved in 200 µl of a dimethylformamide solution to obtain solution B. Solution B was added dropwise to solution A while stirring with a stirrer, and the mixed solution was reacted at 30° C. for 30 minutes. Then, the resulting solution was purified on a Sephadex-G-25 column (1.5 cm×20 cm) using 0.1 M phosphate buffer (pH 6.5)–0.1 M NaCl as an eluent to obtain bovine serum albumin into which a maleimido group was introduced.

The peptide (5 mg) was dissolved in 0.1 M phosphate buffer-5 mM ethylenediaminetetraacetic acid (EDTA), and maleimido group-introduced bovine serum albumin (20 mg) was added thereto (to a total amount of 5 ml or less), followed by reaction at 30° C. for 60 minutes. PBS was added thereto to bring the volume to 12 ml, thereby obtaining a conjugate of the peptide and bovine serum albumin.

(3) The conjugate of the peptide and hemocyanin obtained in the above (1) was thoroughly mixed with Freund's complete adjuvant, and rabbits were subcutaneously injected with the resulting mixture. Thereafter, the conjugate of the peptide and bovine serum albumin obtained in the above (2) was mixed with Freund's complete adjuvant, and the same rabbits were injected with the resulting mixture every two weeks. The blood collected from the rabbits immunized by the above-mentioned method was centrifuged to obtain a human BTC peptide antibody (polyclonal antibody).

The antibodies of the present invention neutralize biological activity of the human BTC protein or a mutein thereof, and bind to the protein or a mutein thereof with high sensitivity and high specificity. They can be therefore used as therapeutic agents for diseases such as arterial sclerosis and cancers. They can be also used as reagents for detecting and assaying human BTC protein or a mutein thereof, and also used as a diagnostic agent for diabetes or complications thereof.

What is claimed is:

1. A monoclonal antibody which (a) specifically binds to a human betacellulin protein comprising the amino acid sequence of SEQ ID NO:1, (b) specifically recognizes amino acid 31 (Arg) to amino acid 80 (Tyr) of SEQ ID NO:1, (c) neutralizes the cell growth stimulating activity of the human betacellulin protein, (d) does not cross-react with at least human epidermal growth factor, human transforming growth factor a, or mouse betacellulin protein, (e) belongs to the immunoglobulin class of IgG, and (f) is produced by cell lines, Mouse 1A1 (FERM BP 5393), Mouse 2B2 (FERM BP 5394) or Mouse 5E5 (FERM BP 5395).

2. A cloned hybridoma which is obtained from a fusion of a homogeneic or heterogeneic lymphocyte, and a mammalian spleen cell immunized by a human betacellulin protein comprising the amino acid sequence of SEQ ID NO:1, and produces the monoclonal antibody of claim 1.

3. A method of producing a monoclonal antibody which comprises:
    proliferating the hybridoma of claim 2 in a liquid culture medium or in an abdominal cavity of a mammal to produce and accumulate the monoclonal antibody, and
    collecting the monoclonal antibody from the liquid culture medium or the abdominal cavity of the mammal to obtain the monoclonal antibody.

4. A composition which comprises an effective amount of the monoclonal antibody according to claim 1, and a carrier, excipient or diluent.

5. A kit for detecting and assaying a human betacellulin protein, which comprises an effective amount of the monoclonal antibody according to claim 1, said human betacellulin protein comprising the amino acid sequence of SEQ ID NO:1.

6. A hybridoma which produces the monoclonal antibody of claim 1.

7. A method of detecting and assaying a human betacellulin protein, which comprises contacting the monoclonal antibody according to claim 1 with a specimen to detect and assay the human betacellulin protein in the specimen, said human betacellulin protein comprising the amino acid sequence of SEQ ID NO:1.

8. A method of purifyng a human betacellulin protein, which comprises contacting the monoclonal antibody according to claim 1 with a crude sample containing the human betacellulin protein, and isolating the human betacellulin protein, said human betacellulin protein comprising the amino acid sequence of SEQ ID NO:1.

* * * * *

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 80 amino acid residues (B) TYPE: amino acid
            (C) STRANDEDNESS: n/a
            (D) TOPOLOGY: linear (ii) MOLECULE TYPE: protein (xi) SEQUENCE DESCRIPTION: SEQ ID NO: 1:

```
Asp Gly Asn Ser Thr Arg Ser Pro Glu Thr Asn Gly Leu Leu Cys Gly
 1               5                  10                  15

Asp Pro Glu Glu Asn Cys Ala Ala Thr Thr Thr Gln Ser Lys Arg Lys
                20                  25                  30

Gly His Phe Ser Arg Cys Pro Lys Gln Tyr Lys His Tyr Cys Ile Lys
            35                  40                  45

Gly Arg Cys Arg Phe Val Val Ala Glu Gln Thr Pro Ser Cys Val Cys
 50                  55                  60

Asp Glu Gly Tyr Ile Gly Ala Arg Cys Glu Arg Val Asp Leu Phe Tyr
 65                  70                  75                  80
```

(2) INFORMATION FOR SEQ ID NO: 2:

(i) SEQUENCE CHARACTERISTICS:
            (A) LENGTH: 1271 base pairs
            (B) TYPE: nucleic acid
            (C) STRANDEDNESS: double
            (D) TOPOLOGY: linear (ii) MOLECULE TYPE: DNA (genomic)

(vi) ORIGINAL SOURCE:
            (A) ORGANISM: Homo sapiens
            (B) STRAIN: MCF7
            (C) INDIVIDUAL ISOLATE: Breast Adenocarcinoma Cell (ix) FEATURE:
            (A) NAME/KEY: CDS
            (B) LOCATION: 295..828

(ix) FEATURE:
            (A) NAME/KEY: mat-peptide
            (B) LOCATION: 388..828

(xi) SEQUENCE DESCRIPTION: SEQ ID NO: 2:

```
CAGCGTGGAG GCTCCAAGGA CCAAGTCCTG CGCCTCTTTG GCGGGGTGTG TGCAGGAGGA        60

GGGGGGATAA ATAGGAGGCT CCCTCCTCCC GGCGACATTC ACGGAGCCGG CCGGCCTCC        120

GCCCTGGGTG TTTCCCTGCC TTGTAGCCAG GGTGCCAGCC TGGGAAGTAG TTTCGTTTC        180

TTCTGCCTCC GGGATTAGTT TCCAGGCACC CTCTCAGGCG CCCGAGGCCC GGGAAGGGG        240

CGAAGAAGGA GGGAGACTTG TCTAGGGGCT GCCCGGCCCG GCAGAGCGGG GTTG ATG        297
                                                             Met
                                                             -31

GAC CGG GCC GCC CGG TGC AGC GGC GCC AGC TCC CTG CCA CTG CTC CTG        345
Asp Arg Ala Ala Arg Cys Ser Gly Ala Ser Ser Leu Pro Leu Leu Leu
-30                 -25                 -20                 -15

GCC CTT GCC CTG GGT CTA GTG ATC CTT CAC TGT GTG GTG GCA GAT GGG        393
Ala Leu Ala Leu Gly Leu Val Ile Leu His Cys Val Val Ala Asp Gly
            -10                  -5                   1

AAT TCC ACC AGA AGT CCT GAA ACT AAT GGC CTC CTC TGT GGA GAC CCT        441
Asn Ser Thr Arg Ser Pro Glu Thr Asn Gly Leu Leu Cys Gly Asp Pro
             5                  10                  15

GAG GAA AAC TGT GCA GCT ACC ACC ACA CAA TCA AAG CGG AAA GGC CAC        489
Glu Glu Asn Cys Ala Ala Thr Thr Thr Gln Ser Lys Arg Lys Gly His
         20                  25                  30

TTC TCT AGG TGC CCC AAG CAA TAC AAG CAT TAC TGC ATC AAA GGG AGA        537
Phe Ser Arg Cys Pro Lys Gln Tyr Lys His Tyr Cys Ile Lys Gly Arg
```

```
                    35                    40                   45                        50
TGC CGC TTC GTG GTG GCC GAG CAG ACG CCC TCC TGT GTC TGT GAT GAA          585
Cys Arg Phe Val Val Ala Glu Gln Thr Pro Ser Cys Val Cys Asp Glu
                        55                        60                   65

GGC TAC ATT GGA GCA AGG TGT GAG AGA GTT GAC TTG TTT TAC CTA AGA          633
Gly Tyr Ile Gly Ala Arg Cys Glu Arg Val Asp Leu Phe Tyr Leu Arg
                70                        75                       80

GGA GAC AGA GGA CAG ATT CTG GTG ATT TGT TTG ATA GCA GTT ATG GTA          681
Gly Asp Arg Gly Gln Ile Leu Val Ile Cys Leu Ile Ala Val Met Val
            85                        90                       95

GTT TTT ATT ATT TTG GTC ATC GGT GTC TGC ACA TGC TGT CAC CCT CTT          729
Val Phe Ile Ile Leu Val Ile Gly Val Cys Thr Cys Cys His Pro Leu
        100                       105                      110

CGG AAA CGT CGT AAA AGA AAG AAG AAA GAA GAA GAA ATG GAA ACT CTG          777
Arg Lys Arg Arg Lys Arg Lys Lys Lys Glu Glu Glu Met Glu Thr Leu
115                     120                      125                      130

GGT AAA GAT ATA ACT CCT ATC AAT GAA GAT ATT GAA GAG ACA AAT ATT          825
Gly Lys Asp Ile Thr Pro Ile Asn Glu Asp Ile Glu Glu Thr Asn Ile
                    135                       140                      145

GCT TAAAAGGCTA TGAAGTTACC TCCAGGTTGG TGGCAAGCTG CAAAGTGCCT               878
Ala

TGCTCATTTG AAAATGGACA GAATGTGTCT CAGGAAAAAC AGCTAGTAGA CATGAATTT         938

AAATAATGTA TTTACTTTTT ATTTGCAACT TTAGTTTGTG TTATTATTTT TTAATAAGA         998

CATTAATTAT ATGTATATTG TCTAGTAATT GGGAAAAAAG CAACTGGTTA GGTAGCAA         1058

ACAGAAGGGA AATTTCAATA ACCTTTCACT TAAGTATTGT CACCAGGATT ACTAGTCA         1118

CAAAAAAGAA AAGTAGAAAG GAGGTTAGGT CTTAGGAATT GAATTAATAA TAAAGCTA         1178

ATTTATCAAG CATTTACCAT GTGCTAATAA GTTTGAAATA TATTATTTCC TTTATTCC         1238

TCAGCAATCC ATGAGATAGC TATTATAATC CTC                                    1271

(2) INFORMATION FOR SEQ ID NO: 3:

(i) SEQUENCE CHARACTERISTICS:
        (A) LENGTH: 80 amino acid residues
        (B) TYPE: amino acid
        (C) STRANDEDNESS: n/a
        (D) TOPOLOGY: linear (ii) MOLECULE TYPE: protein (xi) SEQUENCE DESCRIPTION: SEQ ID NO: 3:

Asp Gly Asn Thr Thr Arg Thr Pro Glu Thr Asn Gly Ser Leu Cys Gly
  1               5                   10                  15

Ala Pro Gly Glu Asn Cys Thr Gly Thr Thr Pro Arg Gln Lys Val Lys
            20                  25                  30

Thr His Phe Ser Arg Cys Pro Lys Gln Tyr Lys His Tyr Cys Ile His
        35                  40                  45

Gly Arg Cys Arg Phe Val Val Asp Glu Gln Thr Pro Ser Cys Ile Cys
    50                  55                  60

Glu Lys Gly Tyr Phe Gly Ala Arg Cys Glu Arg Val Asp Leu Phe Tyr
65                  70                  75                  80

(2) INFORMATION FOR SEQ ID NO: 4:

(i) SEQUENCE CHARACTERISTICS:
        (A) LENGTH: 178 amino acid residues
        (B) TYPE: amino acid
        (C) STRANDEDNESS: n/a
        (D) TOPOLOGY: linear
```

(ii) MOLECULE TYPE: protein (xi) SEQUENCE DESCRIPTION: SEQ ID NO: 4:

| Met | Asp | Arg | Ala | Ala | Arg | Cys | Ser | Gly | Ala | Ser | Ser | Leu | Pro | Leu | Leu |
|-----|-----|-----|-----|-----|-----|-----|-----|-----|-----|-----|-----|-----|-----|-----|-----|
| -31 | -30 |     |     |     | -25 |     |     |     | -20 |     |     |     |     |     |     |

| Leu | Ala | Leu | Ala | Leu | Gly | Leu | Val | Ile | Leu | His | Cys | Val | Val | Ala | Asp |
|-----|-----|-----|-----|-----|-----|-----|-----|-----|-----|-----|-----|-----|-----|-----|-----|
| -15 |     |     |     |     | -10 |     |     |     |     | -5  |     |     |     |     | 1   |

| Gly | Asn | Ser | Thr | Arg | Ser | Pro | Glu | Thr | Asn | Gly | Leu | Leu | Cys | Gly | Asp |
|     |     |     | 5   |     |     |     |     | 10  |     |     |     |     | 15  |     |     |

Pro Glu Glu Asn Cys Ala Ala Thr Thr Thr Gln Ser Lys Arg Lys Gly
          20              25              30

His Phe Ser Arg Cys Pro Lys Gln Tyr Lys His Tyr Cys Ile Lys Gly
         35              40              45

Arg Cys Arg Phe Val Val Ala Glu Gln Thr Pro Ser Cys Val Cys Asp
 50              55              60              65

Glu Gly Tyr Ile Gly Ala Arg Cys Glu Arg Val Asp Leu Phe Tyr Leu
              70              75              80

Arg Gly Asp Arg Gly Gln Ile Leu Val Ile Cys Leu Ile Ala Val Met
              85              90              95

Val Val Phe Ile Ile Leu Val Ile Gly Val Cys Thr Cys Cys His Pro
             100             105             110

Leu Arg Lys Arg Arg Lys Arg Lys Lys Glu Glu Met Glu Thr
    115             120             125

Leu Gly Lys Asp Ile Thr Pro Ile Asn Glu Asp Ile Glu Glu Thr Asn
130             135             140             145

Ile Ala (2) INFORMATION FOR SEQ ID NO: 5:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

TATGGATGGG            10

(2) INFORMATION FOR SEQ ID NO: 6:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:

AATTCCCATC CA          12

(2) INFORMATION FOR SEQ ID NO: 7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear

```
        (ii) MOLECULE TYPE: DNA (xi) SEQUENCE DESCRIPTION: SEQ ID NO: 7:

ATACATATGG ATGGGAATTC CA                                            22

(2) INFORMATION FOR SEQ ID NO: 8:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 8:

CCGGATCCTA GTAAAACAAG TCAACTCT                                      28

(2) INFORMATION FOR SEQ ID NO: 9 :

(i) SEQUENCE CHARACTERISTICS:
            (A) LENGTH: 20 amino acid residues
            (B) TYPE: amino acid
            (C) STRANDEDNESS: n/a
            (D) TOPOLOGY: linear (ii) MOLECULE TYPE: protein (xi) SEQUENCE DESCRIPTION: SEQ ID NO: 9:

Asp Gly Asn Xaa Thr Arg Ser Pro Glu Thr Asn Gly Leu Leu Xaa Gly
 1               5                  10                  15

Asp Pro Glu Glu
         20

(2) INFORMATION FOR SEQ ID NO: 10 :

(i) SEQUENCE CHARACTERISTICS:
            (A) LENGTH: 20 amino acid residues
            (B) TYPE: amino acid
            (C) STRANDEDNESS: n/a
            (D) TOPOLOGY: linear (ii) MOLECULE TYPE: protein (xi) SEQUENCE DESCRIPTION: SEQ ID NO: 10:

Arg Lys Gly Xaa Phe Ser Arg Xaa Pro Lys Gln Tyr Lys His Tyr Xaa
 1               5                  10                  15

Ile Lys Gly Arg
         20
```